(12) United States Patent
Morishita et al.

(10) Patent No.: US 7,164,044 B2
(45) Date of Patent: Jan. 16, 2007

(54) PROCESS FOR PRODUCING HIGH PURITY TRIALKANOLAMINE

(75) Inventors: Fumiaki Morishita, Tokyo (JP); Atsushi Tojo, Yokohama (JP); Takahiro Takinami, Yokohama (JP); Yutaka Sugiyama, Yokohama (JP)

(73) Assignee: Nippon Shokubai Co., Ltd., Osaka (JP)

( * ) Notice: Subject to any disclaimer, the term of this patent is extended or adjusted under 35 U.S.C. 154(b) by 39 days.

(21) Appl. No.: 10/770,297

(22) Filed: Feb. 2, 2004

(65) Prior Publication Data

US 2004/0158102 A1    Aug. 12, 2004

(30) Foreign Application Priority Data

Feb. 3, 2003 (JP) .............................. 2003-026072
Jun. 17, 2003 (JP) .............................. 2003-171784

(51) Int. Cl.
C07C 213/04 (2006.01)
C07C 213/10 (2006.01)

(52) U.S. Cl. ...................................... 564/475; 564/497

(58) Field of Classification Search ................ 564/475, 564/497
See application file for complete search history.

(56) References Cited

U.S. PATENT DOCUMENTS 2,512,584 A * 6/1950 Smith ........................ 203/53
2,512,585 A * 6/1950 Smith ........................ 203/62
3,207,790 A * 9/1965 Matheson et al. .......... 564/497
3,453,183 A * 7/1969 Okubo et al. ............... 203/33
3,849,262 A * 11/1974 Cocuzza ..................... 203/38
4,395,311 A * 7/1983 McDonald .................. 203/34
4,673,762 A * 6/1987 Paslean et al. .............. 564/497
5,292,958 A * 3/1994 Claud et al. ................ 564/499
5,693,866 A * 12/1997 Roling et al. ............... 564/497
6,169,207 B1   1/2001 Tsuneki et al. ............. 564/475
6,291,715 B1   9/2001 Rulder et al. ............... 564/497
6,323,371 B1 * 11/2001 Ruider et al. ............... 564/497
6,388,137 B1 * 5/2002 Ruider et al. ............... 564/499
6,683,217 B1 * 1/2004 Brun-Buisson et al. ..... 564/477

FOREIGN PATENT DOCUMENTS

| | | |
|---|---|---|
| EP | 1 081 130 A1 | 3/2001 |
| EP | 1 219 592 A1 | 7/2002 |
| JP | 5-8693 | 2/1993 |

* cited by examiner

*Primary Examiner*—Brian Davis
(74) *Attorney, Agent, or Firm*—Fish & Richardson P.C.

(57) ABSTRACT

A process for producing a high purity trialkanolamine excelling in hue and having an APHA of not more than 40, characterizing by including producing a mixed alkanolamine by the reaction of an alkylene oxide with ammonia; removing low-boiling substances from the mixed alkanolamine; removing high-boiling substances by subjecting the product deprived of the low-boiling substance to vacuum distillation, and redistilling the distillate obtained by the vacuum distillation.

18 Claims, 5 Drawing Sheets

PROCESS FOR PRODUCING HIGH PURITY TRIALKANOLAMINE

BACKGROUND OF THE INVENTION

1. Field of the Invention

This invention relates to a process for producing trialkanolamines by the reaction of an alkylene oxide with liquefied ammonia in the presence of a zeolite catalyst. More particularly, this invention relates to a process for producing a high purity trialkanolamine excellent in hue by two-stage vacuum distillation of a crude trialkanolamine.

Further, this invention relates to a process for refining a trialkanolamine from a mixed alkanolamine obtained by the reaction of an alkylene oxide with ammonia. More particularly, this invention relates to a process for adding a low-boiling compound to a raw material trialkanolamine and subsequently distilling them together.

2. Description of Related Art

As a commercial way of producing ethanolamine by the reaction of ethylene oxide with ammonia, a process of the reaction of ethylene oxide with aqueous ammonia (aqueous ammonia process) has been in high vogue. This process forms three kinds of product, monoethanolamine, diethanolamine, and triethanolamine. To acquire triethanolamine, therefore, the monoethanolamine, diethanolamine, unreacted ammonia, and water contained, must be separated by vacuum distillation. The crude triethanolamine thus obtained is vacuum distilled because it contains 4–8% of diethanolamine and 0.1–1% of a high-boiling substance. In the distillate recovered, the initial fraction contains diethanolamine and the final or post fraction contains the high-boiling compound both in high concentrations, so that this vacuum distillation produces high purity triethanolamine only in a low yield.

Since the market trend of ethanolamine has changed in recent years, the production balance between diethanolamine and triethanolamine manufactured from the aqueous ammonia process can no longer correspond with the change. To be specific, the demand for diethanolamine, which is used as the raw material for herbicide, is going up greatly, whereas the demand for triethanolamine is reducing on account of the problem of toxicity. To adjust the balance between these demands, a new process other than the aqueous ammonia process for the production of ethanolamine has been developed.

In the production of ethanolamine, a product which is composed of mon-/di-/triethanolamine at a weight ratio of 55/41/4 is obtained by causing ammonia and ethylene oxide to react at a molar ratio of 7:9 while using pentacyl type aluminosilicate (crystal structure MFI type) as a zeolite catalyst (U.S. Pat. No. 6,169,207) (catalyst process).

As a way of reducing coloration in triethanolamine, a process has been proposed which includes heat-treating triethanolamine in the absence of oxygen but in the presence of an inorganic compound such as silicon and aluminum, and subsequently distilling the resultant product (JP-B-05-8693).

SUMMARY OF THE INVENTION

The reaction product obtained by the catalyst process has diethanolamine at a high ratio and triethanolamine at a low ratio. When the product is vacuum distilled to produce triethanolamine, a high purity triethanolamine cannot be obtained because impurities are concentrated into the triethanolamine. There has been the problem that a high purity product cannot be obtained.

Meanwhile, since triethanolamine is used as the raw material for cosmetic preparations, detergents, emulsifiers, etc., it is processed in advance into fatty acid amides and higher alkyl sulfuric esters. It is, therefore, required to possess high purity and avoid inducing coloration to the fullest possible extent during the course of neutralization with inorganic acids such as acetic anhydride, sulfuric acid, and phosphoric acid, and organic acids such as citric acid. Thus, the triethanolamine as a finished product is required to have the prescribed properties.

In accordance with the aqueous ammonia process, a high quality triethanolamine can be obtained by carefully separating the distillation fractions. However, triethanolamine excellent in hue has been produced only in a low yield.

An object of the invention, therefore, is to solve the problem mentioned above and to provide a process for producing a high purity trialkanolamine excellent in hue.

Another object of the invention is to provide a process for refining a trialkanolamine from a mixed alkanolamine obtained by the aqueous ammonia process and/or the catalyst process.

We have repeated a diligent study with a view to solving the problem mentioned above and have perfected the following invention.

This invention concerns a process for producing a high purity trialkanolamine excelling in hue having an APHA of not more than 40, characterized by comprising, in producing a mixed alkanolamine by the reaction of an alkylene oxide with liquid ammonia in the presence of a zeolite type catalyst, or by the reaction of an alkylene oxide with liquid ammonia in the presence of a zeolite type catalyst and the reaction of an alkylene oxide with aqueous ammonia, a step of removing a low-boiling substance for removing unreacted ammonia, water, a monoalkanolamine, and a dialkanolamine from the product of the reaction of an alkylene oxide with ammonia, a step of removing a high-boiling substance by subjecting the product resulting from the removal of the low-boiling substance to a vacuum distillation, and a step for redistilling the distillate resulting from the vacuum distillation.

Further, this invention is directed at a process for refining a trialkanolamine from a mixed alkanolamine obtained by the process mentioned above and is accomplished by a process for refining a trialkanolamine, characterized by adding to the raw material trialkanolamine a low-boiling compound having a boiling point less than the boiling point of the trialkanolamine and distilling them together.

In accordance with this invention, a high purity trialkanolamine excelling in hue can be produced by removing the unreacted ammonia, water, mono-, and diethanolamine from the reaction solution obtained-by the catalyst process or the combined process of the catalyst process and the aqueous ammonia process and subjecting the resulting reaction solution to two stages of vacuum distillation, namely crude distillation and redistillation.

According to this invention, it is possible to heighten the purity of a trialkanolamine and, at the same time, improve the quality in terms of hue by a simple process of adding a low-boiling compound having a boiling point lower than the boiling point of the trialkanolamine to the raw material trialkanolamine and distilling them together. Further, as, regards the quality, an improvement in the test for phosphorus coloration and the test for aging can be confirmed.

BRIEF DESCRIPTION OF THE DRAWINGS

The accompanying drawings incorporated in and forming a part of the specification, illustrate several aspects of the present invention, and together with the description serve to explain the principles of the invention. In the drawings.

DESCRIPTION OF THE PREFERRED EMBODIMENTS

Figure 1:
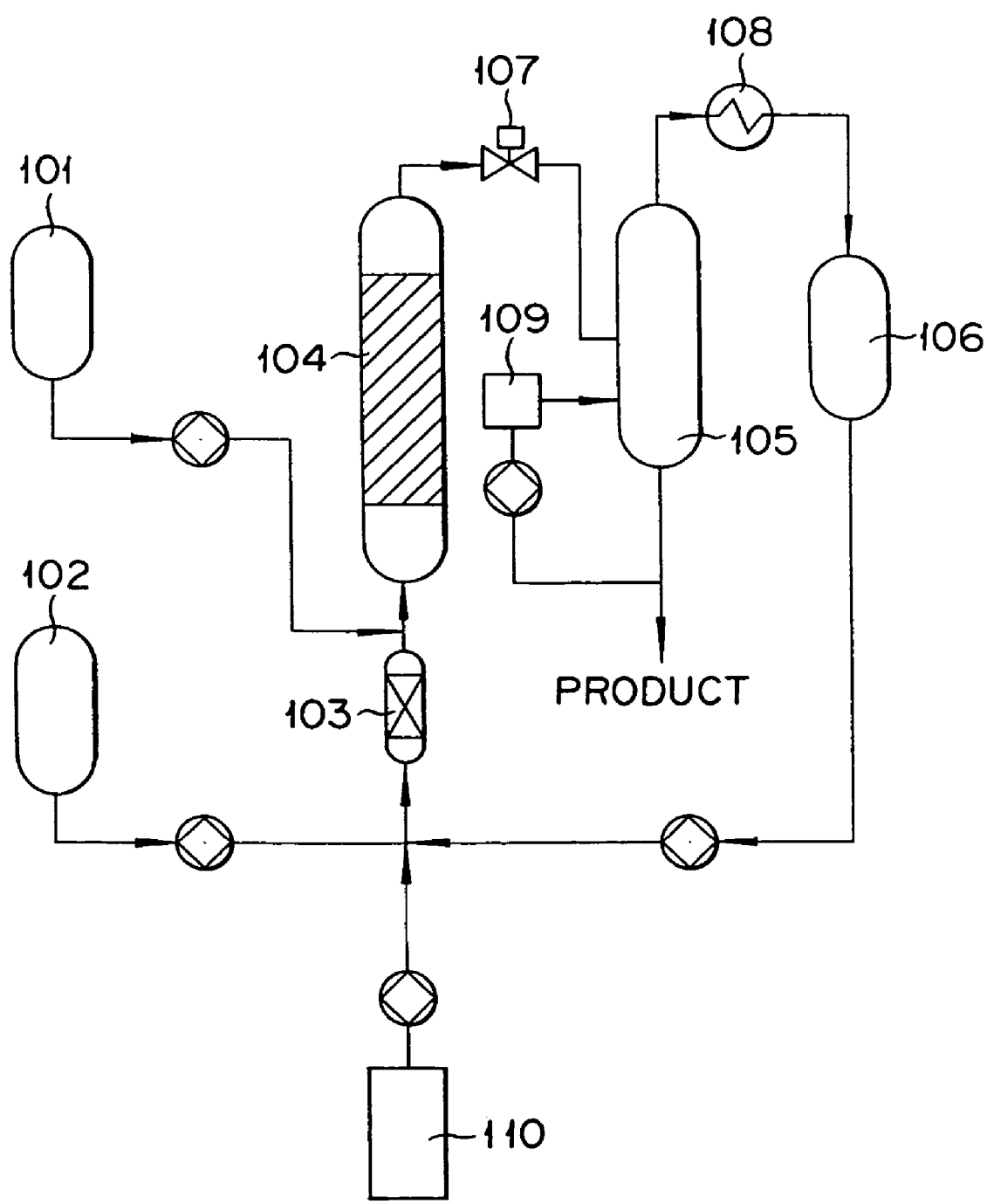
FIG. 1 is an explanatory diagram illustrating an apparatus for producing ethanolamine by the catalyst process which comprises recycling monoethanolamine to a reactor.

The term "alkanolamine" as used in the present specification refers to alkanolamines having a carbon number in the range of 2–5, for instance, ethanolamine and propanolamine. Here, the process for producing such an alkanolamine will be described with respect to ethanolamine as a representative.

The alkanolamine which is obtained by the reaction is a mixture of a monoalkanolamine, a dialkanolamine, and a trialkanolamine.

(Process for Producing a Mixed Ethanolamine by a Reaction of Ethylene Oxide with Liquid-Ammonia in the Presence of a Zeolite Type Catalyst, or by the Reaction of Ethylene Oxide With Liquid Ammonia in the Presence of the Zeolite Type Catalyst and a Reaction of Ethylene Oxide with Aqueous Ammonia)

First, the mixed ethanolamine to be used as the raw material is an ethanolamine solution which is obtained by the reaction of ethylene oxide with liquid ammonia in the presence of a ZSM-5 zeolite as a catalyst (hereinafter may be referred to as "catalyst process" or a mixed solution of the ethanolamine solution obtained by the catalyst process and an ethanolamine solution continuously obtained by the conventional reaction of ethylene oxide with aqueous ammonia (hereinafter maybe referred to as "aqueous ammonia process"). The process contemplated by this invention does not discriminate the produced ethanolamine on account of variations in the ratio of formation and in the ratio of productions by the catalyst process and the aqueous ammonia process.

Next, a) catalyst process and b) a combination of catalyst process and aqueous ammonia process will be explained.

a.) Catalyst Process

The reaction of liquid ammonia and ethylene oxide as raw materials is performed in the state of liquid phase under pressure using a fixed-bed reactor or reaction vessel. The ammonia is used in excess of the theoretical amount of the reaction with ethylene oxide, so that excess ammonia is separated and recovered from the product, and the recovered ammonia is generally supplied again to the reactor. The ethanolamine which is obtained by the reaction is a mixture of monoethanolamine (hereinafter may be referred to as "MEA"), diethanolamine (hereinafter may be referred to as "DEA"), and triethanolamine (hereinafter may be referred to as "TEA"). This mixture may be recycled to the reactor when DEA and TEA are to be obtained selectively. When DEA is to be selectively obtained, it is permissible to separate MEA alone and recycle it to the reactor. Further, when necessary, the mixed solution mentioned above and MEA may be mixed and used for the recycling.

The reactor is a fixed-bed type one in which the raw material is fed generally in an up-flow stream. Further, the reactor is preferred to be of insulation type from the view point of the efficiency of reaction.

Preferably the reaction temperature is in the range of normal temperature–200° C. and the reaction pressure in the range of 8–15 MPa. The liquid of raw materials flows inside the reactor generally not less than 0.1 liter/hr and preferably in the range of 0.1–100,000 liters/hr. At this time, the liquid hourly space velocity (LHSV) is generally in the range of 0.5–100 $hr^{-1}$, depending upon the reaction temperature, the kind of catalyst, and the amount of the catalyst used.

Next, an apparatus to be used for producing ethanolamine by the catalyst process will-be explained. FIG. 1 is an explanatory diagram illustrating an apparatus to be used in this invention for producing ethanolamine by recycling MEA to the reactor. In FIG. 1, liquid ammonia from a liquid ammonia tank 102 is fed to a reactor 104 via a preheater 103, and ethylene oxide from an ethylene-oxide tank 101 is fed to the reactor 104. The ammonia is generally added in the range of 2–30 mols relative to 1 mole of ethylene oxide, though it is not particularly restricted. The preheater 103 is intended to heat the raw materials in advance of the reaction and quicken their arrival at the reactor, so that the temperature of the preheater 103 is preferred to be in the range of 20° C.–100° C. The reaction is an adiabatic reaction.

The product emanating from the reactor 104 is forwarded via a pressure control valve 107 to an ammonia recovering column 105 such as a flash drum. The ammonia recovering column 105 is fitted with a reboiler 109. In the ammonia recovering column 105, via the top of the column ammonia is introduced to a cooler 108 and recovered as liquid ammonia in a tank 106 and, at the same time, a mixture of ammonia and ethanolamine is obtained as bottoms in the bottom of the column. In this recovery step, usually 80–98% by weight, preferably 85–96% by weight, and more preferably 90–95% by weight, of the ammonia is recovered in the form of liquid ammonia in the tank 106. Generally, the ammonia recovering column 105 is operated under a pressure in the approximate range of 1–3 MPa, since a cooling water of normal temperature is used as the refrigerant for the cooler 108. The bottoms obtained from the ammonia recovering column 105, therefore, contains about 4–20% by weight of ammonia.

This process involves the step of recycling MEA and, therefore, is required to obtain MEA from the ethanolamine mixture. It enjoys the merit of decreasing the amount of MEA to be recycled, though this separation results in increasing the number of component steps. Incidentally, MEA is separated from the product (the device therefor not shown) and stored in a tank 110.

The position at which the MEA is recycled to the reactor is preferred to be the inlet to the preheater from the viewpoint of the efficiency of the reaction.

The ethylene oxide concentration at the inlet to the reactor is generally in the range of 3–35% by weight, preferably 5–30% by weight, and most preferably 8–25% by weight. If the ethylene oxide concentration is unduly low, the shortage will degrade the productivity excessively and decrease the amount of DEA to be obtained.

Figure 2:
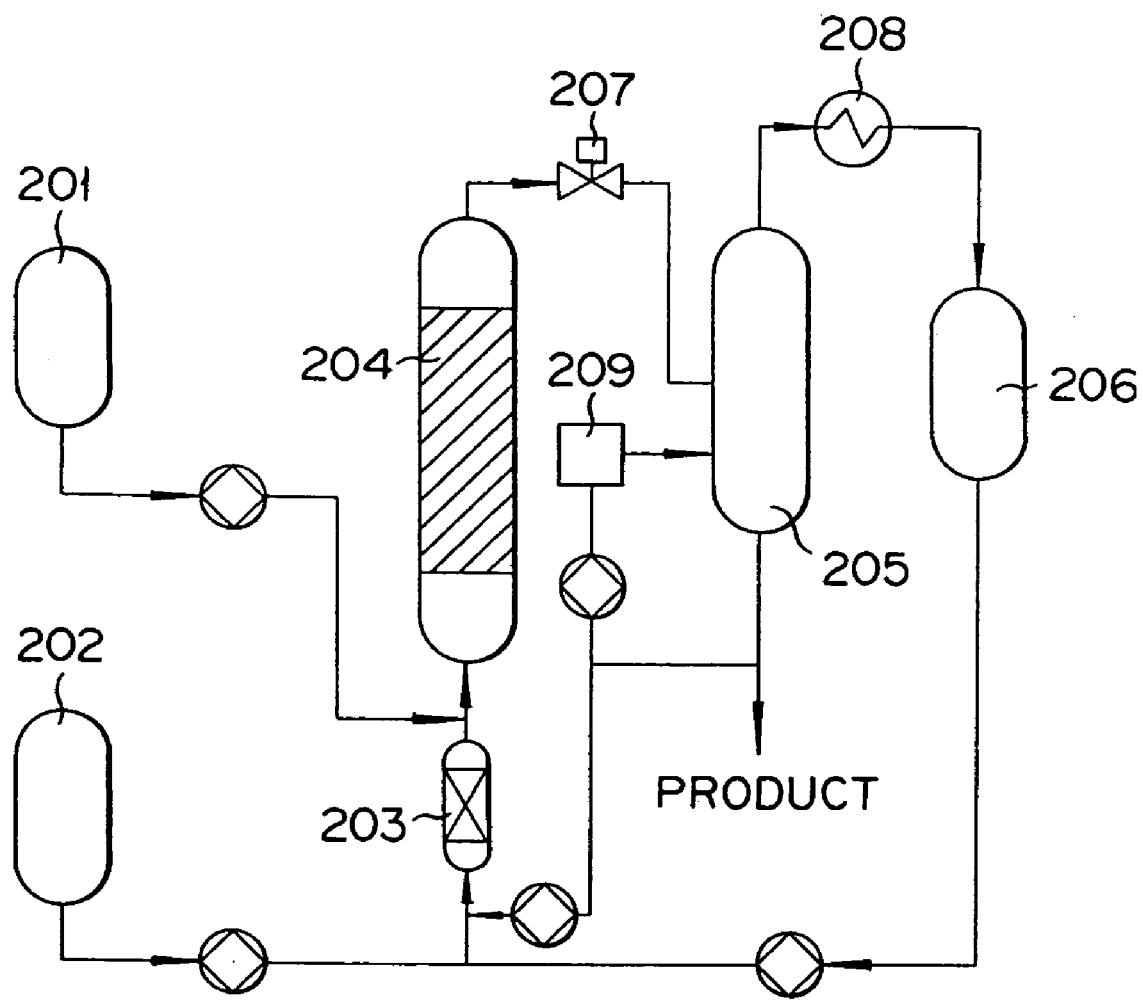
FIG. 2 is an explanatory diagram illustrating an apparatus for producing ethanolamine by the catalyst process.

FIG. 2 is an explanatory diagram illustrating an apparatus to be used in this invention for producing ethanolamine by recycling part of the liquid product from which the greater part of the unaltered ammonia has been removed. In FIG. 2, the same members and devices as those in FIG. 1 are denoted by reference numerals which are formed by substituting 2 for 1 at the third decimal position of the relevant reference numerals used in FIG. 1 unless otherwise specified.

In FIG. 2, part of the bottoms from an ammonia recovering column 205 or the liquid product is fed to a reactor 204 or a preheater 203. The liquid product contains MEA, DEA, and TEA, and ammonia. By recycling this mixture to the reactor 204 and subjecting it to reaction again therein, a product having a high concentration of DEA can be obtained.

The liquid product is generally recycled in the range of 5–90% by volume, preferably 10–80% by volume, and more preferably 20–70% by volume, based on the total product. If the amount of the liquid to be recycled is unduly small, the shortage will prevent the ethylene oxide concentration from being increased, thereby the amount of DEA to be obtained being increased. Conversely, if the amount of the liquid to be recycled is unduly large, the excess will result in unduly increasing the amount of the liquid flowing through the inlet to the reactor relative to the amount of the product, thereby degrading the efficiency of production.

Further, part of the liquid product is preferably recycled to the reactor without completely separating ammonia from the ethanolamine. Complete separation of ammonia requires the pressure to fall in the range of normal pressure —reduced pressure and this decrease of pressure is very expensive.

b) A Combination of catalyst process and aqueous ammonia process

Figure 3:
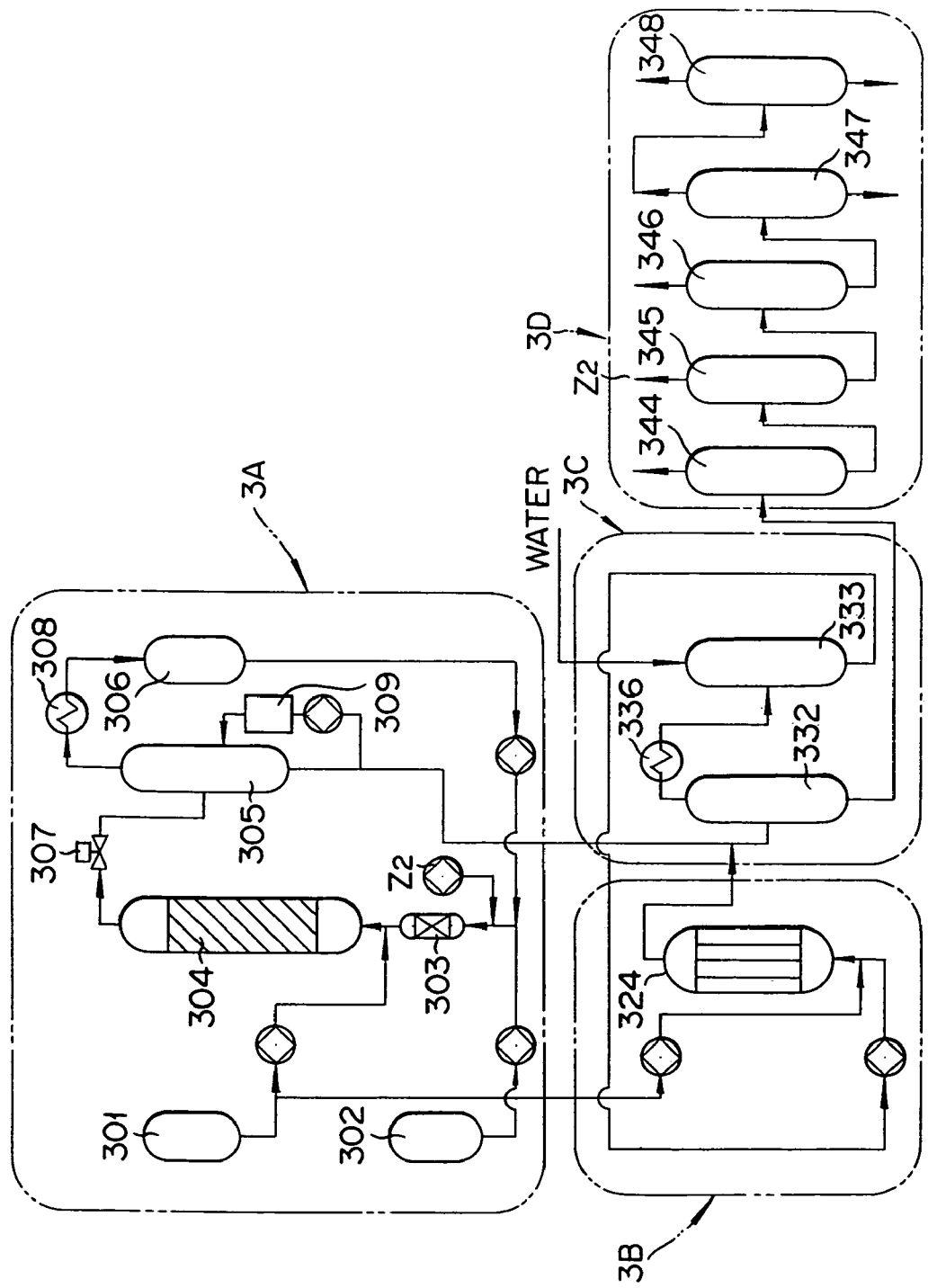
FIG. 3 is a diagram illustrating a flow sheet of the process for producing ethanolamine by the combination of the catalyst process and the aqueous ammonia process.

FIG. 3 is a diagram illustrating a flow sheet of the process for producing ethanolamine by the combination of catalyst process and aqueous ammonia process. In FIG. 3, the block 3A depicts the flow of the process for producing ethanolamine by catalyst process, the block 3B the process for producing ethanolamine by aqueous ammonia process, the block 3C the ammonia recovery system, and the block 3D the refinery system.

As regards the process for producing ethanolamine by catalyst process, the reaction is performed by using liquid ammonia and ethylene oxide as raw materials in the state of a liquid phase under pressure using a fixed-bed reactor. The ammonia is generally used in the range of 2–30 mols per 1 mol of ethylene oxide. Since the ammonia is used in excess of the theoretical amount of the reaction with ethylene oxide, ammonia is separated and recovered from the product and fed again to the reactor. The ethanolamine which is obtained by the reaction is a mixture of MEA, DEA, and TEA. In the case of obtaining DEA and TEA selectively, the mixture may be recycled to the reactor. In the case of obtaining DEA selectively, MEA alone may be separated and recycled to the reactor.

A reactor, and reaction conditions such as reaction temperature, pressure, flow rate, and LHSV to be used in b) are the same to the catalyst process.

In FIG. 3, from a raw material liquid ammonia tank 302 and a liquid ammonia tank 306, liquid ammonia is fed by a high-pressure pump to a reactor 304 via a preheater (20° C.–100° C.) 303. In the meantime, EO (ethylene oxide) from an EO tank 301 is fed by a high-pressure pump to the reactor 304. The reactor 304 is maintained under a pressure in the approximate range of 8–15 MPa by a pressure control valve 307. The product which has emanated from the pressure control valve 307 is forwarded to the middle stage of an ammonia recovering column 305, which is controlled to a pressure in the approximate range of 1–3 MPa. The ammonia recovering column 305 is fitted with a reboiler 309. The ammonia which has emanated from the top of the ammonia recovering column 305 is cooled in a cooler (using normal cooling water as a refrigerant) 308 and recovered in the liquid ammonia tank 306. The bottom of the ammonia recovering column 305 contains ethanolamine mixture and 4–20% by weight of ammonia. The bottom is forwarded to an ammonia stripping column 332 for aqueous ammonia process.

Meanwhile, a process for producing ethanolamine by the aqueous ammonia process using aqueous ammonia as a raw material maybe effected by any of the well-known process. For example, aqueous ammonia from an aqueous ammonia tank 333 and EO from the EO tank 301 are forwarded to a reactor 324. The amounts of ammonia and EO to be used may be properly set to suit the purpose of use, since the ratio of MEA, DEA, and TEA to be obtained varies with the ratio of ammonia and EO used. The amount of ammonia in the range of 1–40 mols per mol of EO may be cited for example. The reaction is generally carried out in a shell-and-tube type reactor under a pressure in the range of normal pressure—16 MPa at a reaction temperature in the range of normal temperature—150° C. The reaction solution which contains ammonia/water/ethanolamine is mixed with the bottoms of the ammonia recovering column 305 mentioned above and forwarded to the middle stage of the ammonia stripping column 332.

In the ammonia stripping column 332, ammonia and water are released via the top of the column and recovered via a cooler 336 into the aqueous ammonia tank 333. The resultant aqueous ammonia is diluted and reclaimed as a raw material for-the reaction of the aqueous ammonia process.

The bottoms from the ammonia stripping column 332 may be refined in a refinery system 3D. The bottoms contain water and ethanolamine. The bottoms are fed into a dehydrating column 344, wherein water is removed via the top of the column and the bottoms are fed into a MEA rectifying column 345. The liquid from the top of the MEA rectifying column 345 is partly introduced via a pump to the preheater 303. The reference numerals 346, 347, and 348 respectively denote a DEA rectifying column, a TEA distilling column, and a TEA rectifying column. The amount of MEA to be recycled depends on the DEA to be aimed at. In order to clarify the operation relating to the recycle of MEA, the whole process including not only the system for the preparation of ethanolamine but also the refining system has been explained. The process contemplated by this invention does not discriminate the produced ethanolamine on account of a variation in the ratio of formation and in the ratio of productions by the catalyst process and the aqueous ammonia process.

(Removing a Low-Boiling Substance for Removing Ammonia, Water, MEA, and DEA from the Product)

From the liquid ethanolamine mixture, ammonia, water, MEA, and DEA are separated by a well-known process so as to obtain a raw material solution for TEA. The separation, for which various well-known processes may be available, may be implemented as follows.

The ammonia in the liquid mixture is removed by pressure distillation. In the distillation, the temperature and the pressure are generally in the respective ranges of 100° C.–160° C. and 3.0–1.0 MPa. The pressure distillation is generally carried out for duration of 0.1–2 hours. In the ammonia recovery system 3C shown in FIG. 3, ammonia is recovered from the bottoms of the ammonia recovering column 305.

Further, the ammonia, water, MEA and DEA, which have been recovered in the above process, are subjected to vacuum distillation to be expelled. In the vacuum distillation, the temperature and the pressure are generally in the respective ranges of 135° C.–180° C. and 5.33–0.53 kPa. This vacuum distillation is generally performed for duration of 0.5–36 hours. Incidentally, for the distillation, a plate column, a packed column, wetted-wall column, or spray column is generally adopted. In the refinery system 3D shown in FIG. 3, the bottoms from the ammonia stripping column 332 are fed into the dehydrating column 344. In the dehydrating column 344, water is removed through the top of the column and the bottoms are fed into the MEA rectifying column 345. The bottoms from the MEA rectifying column 345 are fed into the DEA rectifying column 346. Incidentally, MEA and DEA, when necessary, may be subjected to distillation again.

The raw material solution for TEA is obtained in the form of bottoms from the distillation column and is used as the liquid raw material for the next step of crude distillation. It is preferred to contain 96–70% by weight of TEA, not more than 10% by weight of DEA, and not more than 15% by weight of a high-boiling compound.

(Removal of a High-Boiling Substance by Vacuum Distillation of Product After Removal of the Low-Boiling Substance)

A distillate is obtained as crude TEA by a crude distillation. The crude distillation is performed continuously or batchwise. The continuous distillation is preferred over the batch distillation from the viewpoint of the productivity. The atmosphere which fills the distillation vessel and overlays the raw material solution is preferably displaced with an insert gas such as nitrogen and helium prior to the distillation. This displacement is preferred because the removal of an oxidative gas such as oxygen results in preventing the raw material solution from yielding to subsequent reactions. The working temperature/pressure of this distillation is generally in the range of 120° C.–210° C./0.05–1.80 kPa and preferably in the range of 130° C.–200° C./0.05–1.20 kPa. The operating time of the distillation is generally in the range of 0.5–36 hours and preferably in the range of 0.5–24 hours. Though a plate column, a packed column, a wetted-wall column, or a spray column is generally adopted, the use of a packed column, which is filled with fillers, has disabled not only the production of high purity TEA but also the impartation of the prescribed properties to the product As a result of various studies, we have found that the use of an empty column, not filled with fillers, enables. TEA to be produced as aimed at. The crude TEA preferably contains 97–85% by weight of TEA, not more than 10% by weight of DEA, and not more than 5% by weight of a high-boiling compound. In the refinery system 3D shown in FIG. 3, the bottoms from the DEA rectifying column 346 are fed into a TEA distilling column 347.

(Redistilling the Distillate Obtained in the Vacuum Distillation)

The redistillation is generally carried out batchwise using an empty column, not filled with fillers. The crude TEA, which is the raw material for the redistillation, contains a low-boiling compound such as DEA and a high-boiling compound based on the boiling point of TEA in considerable proportions. That is, the low-boiling compound and the high-boiling compound are preferred to be removed efficiently. Thus, by adopting the batch operation instead of the continuous operation, removing the low-boiling compound as an initial fraction, and removing the high-boiling compound as a post fraction, it is possible to obtain the remaining intermediate fraction as the TEA of a high quality. In this batch distillation, by continuously or intermittently testing the distillate for purity by analytical means such as gas chromatography, it is possible to control the purity of the product based on the results of the analysis.

When the crude TEA is placed in the distillation device to be vacuum distilled, the intermediate fraction excluding the initial fraction containing the low-boiling compound and the post fraction containing the high-boiling compound is obtained as TEA of a high quality. The operating temperature/pressure during the distillation is generally in the range of 100° C.–200° C./0.05–1.20 kPa and preferably in the range of 120° C.–190° C./0.05–0.80 kPa. The operating time of the distillation is generally in the range of 0.5–36 hours and preferably in the range of 0.5–24 hours. In the refinery system 3D shown in FIG. 3, the distillate emanating from the TEA distilling column 347 (may referred to as "OH solution" ) is fed into a TEA redistilling column 348 to obtain a high purity TEA.

The TEA of a high quality thus obtained generally exhibits the following properties: Purity of not less than 98% and preferably not less than 99%, hue (APHA) of not more than 40 and preferably not more than 25, and absorbance determined by the test for phosphorus coloration generally of not more than 0.12, 0.06, and 0.08 and preferably of not more than 0.10, 0.04, and 0.06 respectively at wavelengths of 420, 510, and 530 nm.

Another embodiment of the present invention will be explained below.

(Preparation of Ethanolamine)

As commercial ways of producing ethanolamine, a) catalyst process and b) a combination of catalyst process and aqueous ammonia process, which are described above, may be cited.

FIG. 3 is a diagram illustrating a flow sheet of the process for producing ethanolamine by the combination of the catalyst process and the aqueous ammonia process. In accordance with the procedure in FIG. 3, ethanolamine can be obtained.

(Preparation of Raw Material TEA)

The ethanolamine obtained as described above (at the inlet to the ammonia stripping column 332) contains MEA, DEA, TEA, ammonia as the unaltered raw material, and water. Here, the TEA as the raw material is obtained by expelling ammonia, water, MEA, and DEA sequentially in the order mentioned from the ethanolamine by fractional distillation. The distillation regarding water, MEA, and DEA is performed using any of well known apparatuses and processes.

Specifically, water, MEA, and DEA are expelled respectively by vacuum distillation. The temperature and the pressure for vacuumizing the distillation device are generally in the respective ranges of 55° C.–180° C. and 110–5.3 hPa. The operating time of the vacuum distillation is generally in the range of 0.5–36 hours. A plate column, a packed column, a wetted-wall column, or a spray column is generally adopted for the distillation.

The raw material TEA is obtained as the bottoms from the DEA distilling column. It generally has a composition of 96–85% by weight of TEA, not more than 10% by weight of DEA, and not more than 15% by weight of a high-boiling compound.

(Distillation of Raw Material TEA)

The raw material TEA obtained as described above and a low-boiling compound having a boiling point lower than the boiling point of TEA (hereinafter abbreviated as "low-boiling compound" are added together and subjected to distillation. Here, the boiling point of TEA is 360° C. Examples of low-boiling compounds may include various forms of water such as distilled water and deionized water; alcohols such as ethanol, methanol (anhydrous) or (hydrous), propyl alcohol, isopropyl alcohol, butyl alcohol, and t-butyl alcohol; ketones such as acetone and methylethyl ketone; esters such as ethylene glycol monoacetate and ethylene glycol monoethyl ether acetate; diols such as monoethylene glycol and diethylene glycol; and halogenated hydrocarbons such as carbon tetrachloride. Low-boiling compounds are preferred to have a boiling point less than that of DEA from the viewpoint of quality improvement. Incidentally, the boiling point of DEA is 270° C. Further, the low-boiling compound is preferred to be a compound having a boiling point of not lower than 30° C. from the viewpoint of ease of handling. Among other low-boiling compounds, such low-boiling compounds which exhibit solubility in organic compounds and TEA and assume a liquid state and water prove particularly favorable. Further, the compounds which are obtained by the reaction of synthesis of ethanolamine excluding DEA, water and/or MEA prove advantageous. The compound which is obtained by the reaction of synthesis of ethanolamine is at an advantage in avoiding generation of a new impurity and permitting recycling, as compared with a third substance other than those mentioned above. When water is used as the low-boiling compound, no problem ensues because the distillation gives rise to water as a by-product and the produced TEA contains water in a very small amount.

The low-boiling compound may be added into the raw material TEA in advance of the distillation and mixed together, or the raw material TEA and the low-boiling compound be separately fed to the distilling column with. The addition of the low-boiling compound prior to the distillation proves favorable from the viewpoint of convenience of the operation. The amount of the low-boiling compound to be added is not particularly restricted but only required to bring a discernible effect with respect to the hue and the phosphorus coloration of the refined TEA. The amount is generally in the range of 0.1–1000 parts by weight, preferably 0.5–100 parts by weight, and more preferably 0.5–30 parts by weight, based on 100 parts by weight of the raw material TEA. If this amount is less than 0.1 part by weight, the shortage will prevent the improvement of quality of TEA. Conversely, if this amount exceeds 1000 parts by weight, the excess will prevent the improvement of the quality with proportionately.

The distillation is performed continuously or batchwise. The continuous distillation is preferred over the batch distillation in terms of productivity. The atmosphere which fills the distillation vessel and overlays the liquid raw material is preferred to be displaced with an inert gas such as nitrogen and helium prior to the distillation. This displacement can prevent the liquid raw material from succumbing subsequent reactions by removing an oxidative gas such as oxygen therefrom. The operating temperature/pressure of the distillation is generally in the range of 120° C.–210° C./0.5–18.0 hPa and preferably in the range of 130° C.–200° C./0.5–12.0 hPa. The operating time of the distillation is generally in the range of 0.5–36 hours and preferably in the range of 0.5–24 hours. For the distillation, any of well-known devices such as plate column, packed column, wetted-wall column, and spray column may be adopted. The distillation results in giving a composition formed of 97–85% by weight-of TEA, not more than 10% by weight of DEA, and not more than 5% by weight of the high-boiling compound (referred to occasionally as "crude TEA"). Incidentally, the magnitudes of APHA hue are 85 without addition of the low-boiling compound and about 23 (20–35) with the addition. The magnitudes of phosphorus coloration at a wavelength of 510 nm are 0.20 without addition of the low-boiling compound and 0.03 with the addition.

When the TEA is required to have a higher quality regarding purity, hue, and phosphorus coloration, it is further distilled (hereinafter referred to as "rectification"), as occasion demands, and subjected to a refining treatment.

The resultant raw material TEA to be used for rectification and a low-boiling compound are added together and distilled. The addition process and amount of the low-boiling compound are the same as those mentioned with the distillation above.

The rectification is generally carried out batchwise using an empty column, not packed with fillers. In accordance with this manner, the initial fraction and the post fraction can be removed efficiently. The raw material TEA for the rectification contains a low-boiling compound such as DEA and a high-boiling compound, based on the boiling point of TEA, in considerable proportions. That is, the low-boiling and high-boiling compounds are preferred to be removed efficiently. Thus, by adopting the batch operation instead of the continuous operation, the low-boiling compound is removed as the initial fraction, the high-boiling compound as the post fraction, and the remaining intermediate fraction is obtained as TEA of a high quality. In this batch distillation, it is possible to control the purity of the product based on the results of the analysis by continuously or intermittently testing the distillate by analytical means such as gas chromatography.

When the raw material TEA for the rectification is placed in the distillation device to be vacuum distilled, the intermediate fraction excluding the initial fraction containing the low-boiling compound and the post fraction containing the high-boiling compound is obtained as TEA of a high quality. The operating temperature/pressure of the rectification is generally in the range of 100° C.–200° C./0.5–12.0 hPa and preferably in the range of 120° C.–190° C./0.5–8.0 hPa. The operating time of the rectification is generally in the range of 0.5–36 hours and preferably in the range of 0.5–24 hours.

The TEA of a high quality thus obtained generally exhibits the following properties: Purity of not less than 98% and preferably not less than 99%, hue (APHA) of not more than 40 and preferably not more than 25, and absorbance determined by the test for phosphorus coloration generally of not more than 0.12, 0.06, and 0.08 and preferably of not more than 0.10, 0.04, and 0.06 respectively at wavelengths of 420, 510, and 530 nm.

EXAMPLES

Now, this invention will be described more specifically below with reference to examples and comparative examples. This invention is not restricted in any way by these examples.

(Definition of LHSV)

LHSV(/hr)=(Weight per unit time of reaction solution supplied to reactor (kg/hr))/(weight of catalyst in reactor (kg))

(Analysis)

The analysis of ethanolamine is performed using a gas chromatograph provided with a hydrogen flame ionization detector. This apparatus is fitted with a nonpolar capillary column and the analysis is performed by the internal standard process.

(Hue)

An APHA standard master solution is prepared by accurately weighing out 1.245 g of reagent chemical grade potassium chloroplatinate and 1.00 g of reagent chemical grade cobalt chloride hexahydrate, placing them in a 1000-ml measuring flask. To the flask, are added about 100 ml of deionized water and 100 ml of a reagent chemical grade hydrochloric acid (36% content), then the flask is heated to dissolve the solid. After cooling, to the flask is added deionized water to a total volume of 1000 ml. This is equivalent to APHA No. 500.

To a 100-ml measuring flask is added a prescribed amount of APHA standard master solution, and then deionized water to the capacity. The resultant is used as an APHA standard solution. The APHA No. of this APHA standard solution is 5×V, wherein V denotes the amount (ml) of the standard master solution. The standard solutions are regulated by graduations of APHA No. 5 from 0. These standard solutions are each placed in a glass vessel to a marked line. The vessel is a lidded pipe made of quartz glass or Pyrex in dimensions of 25 mm in outside diameter, 22 mm in inside diameter, and 250 mm in total length, furnished with a flat bottom, which is fused with the pipe. The vessel has the marked line at a height of 130 mm from the bottom surface in order to fix the volume (about 50 ml) of the solution to be contained.

The TEA obtained is placed in the glass vessel of the same as the above till the marked line. This vessel and the vessels containing the APHA standard solutions are placed on a white sheet of paper. Their contents are compared in color through visual observation from above under natural color to determine the hue of the sample.

(Test for Phosphorus Coloration)

In a 100-ml Erlenmeyer flask furnished with a grounded-in stopper, TEA weighing 27 g and deionized water-weighing 3 g are added. To the flask, are added 7.5 g of propylene glycol and 6.0 g of reagent chemical grade phosphoric acid and the flask is mixed by vigorous agitation. The flask is heated by being immersed in a water bath at 75±1° C. for 20 minutes. The flask is withdrawn from the water bath, vigorously shaken, and the left cooling for 20 minutes. After the cooling, the mixture in the flask is stirred again and deaerated by means of a supersonic purifier. Thereafter, the resultant product is tested for absorbance at wavelengths of 420, 510, and 530 nm using a spectrophotometer with a glass-ceramic disk 50 mm in diameter.

(Test for Aging)

TEA weighing 250 g is placed in a bottle made of stainless steel, left standing for two days in an oven kept at 120° C. under an atmosphere of nitrogen, and thereafter tested for change in hue.

Example I-1

In a plant for producing ethanolamine by the catalyst process as illustrated in FIG. 1, EO, liquid ammonia, and ethanolamine were continuously introduced into a reactor packed with a catalyst, till their final concentrations reached 18.1, 70.9, and 11.0% by weight respectively. The reaction was performed under an adiabatic condition, a reaction pressure of 10 MPa, an inlet temperature of 45° C., and an LHSV of 5.9. The catalyst used was a ZSM-5 type zeolite which had undergone ion exchange with lanthanum. The degree of conversion of ethylene oxide in the reaction was nearly 100%.

The resultant reaction solution was subjected to pressure distillation and nitrogen bubbling to expel unaltered ammonia, and subsequently subjected to vacuum distillation to distill off MEA:and DEA. The bottoms thus obtained were found to have a composition formed of 76.6% by weight of TEA, 9.9% by weight of DEA, and 13.5% by weight of a high-boiling compound.

The bottoms (400 g) were placed in a 500 ml three-neck flask made of glass and furnished with a capillary tube and given thorough displacement with nitrogen gas. Thereafter, it was heated and vacuumized and subjected to a crude distillation under the conditions of 175° C.–180° C./0.33–0.21 kPa. The crude TEA solution distilled at this time totaled 348 g, representing a yield of 87.1% based on the amount of the bottoms fed to the flask. Then, the crude TEA solution was found to have a composition formed of 88.0% by weight of TEA, 7.4% by weight of DEA, and 4.6% by weight of the high-boiling compound, indicating a vast decrease of the high-boiling compound. Table 2 shows the conditions of the crude distillation and the amounts of fractions recovered. Table 3 shows the concentrations of the individual fractions and the amounts of the fractions recovered in the crude distillation.

Further, the crude TEA-solution (345 g) were placed in another three-necked flask and given therein thorough displacement with nitrogen-gas. When it was subsequently heated and vacuumized and redistilled under the conditions of 164° C.–173° C./0.26–0.24 kPa, TEA having a purity of 99.0% and weighing 187 g (yield 61.6%) was obtained. Table 4 shows the conditions of the redistillation and the amounts of the fractions recovered. Table 5 shows the concentrations of the individual fractions and the amounts of the fractions recovered.

The TEA thus-obtained was found-to have a hue of 25 and an absorbance determined by the phosphorus coloration test of 0.09, 0.04, and 0.02 at wavelengths respectively of 420, 510, and 530 nm. The sample had a colorless, transparent appearance free of suspended matter and a smell of slight fragrance and not of pungent odor.

Example I-2

Ethanolamine was produced using an apparatus constructed as illustrated in FIG. 3. In the plant for producing ethanolamine by the aqueous ammonia process, the crude MEA obtained in Example I-1, EO, and an aqueous 37% ammonia solution were continuously introduced in such flow rates into the reactor as to allow the molar ratio of EO and ammonia to reach 0.275. In the plant for producing ethanolamine by the catalyst process and the aqueous ammonia process, the reaction was performed with the degree of conversion of EO set at 100%.

The reaction solutions obtained by the catalyst process and the aqueous ammonia process were deprived of unaltered ammonia, and the remaining solutions were mixed. At this time, the mixing ratio of the two solutions was 80:20 (weight) The mixed solution was subjected to vacuum distillation to expel water, MEA, and DEA and to obtain bottoms of the column. The bottoms had a composition formed of 85.3% by weight of TEA, 9.3% by weight of DEA, and 5.4% by weight of a high boiling compound.

The bottoms (800 g) were placed in a 1,000 ml three-neck flask made of glass and furnished with a capillary tube and given therein thorough displacement with nitrogen gas. It was subsequently heated and vacuumized and subjected to a crude distillation under the conditions of 170° C.–180° C./0.33–0.31 kPa. The amount of crude TEA separated by distillation at this time totaled 744 g, representing a yield of 93% based on the amount of the bottoms fed to the column. The crude TEA was found to have a composition formed of 88.9% by weight of TEA, 9.7% by weight of DEA, and 0.8% by weight of the high-boiling compound, indicating a vast decrease of the high-boiling compound. Table 6 shows the conditions for the crude distillation and the amounts of the individual fractions recovered. Table 7 shows the concentrations of the individual fractions and the amounts of the fractions recovered in the crude distillation.

Further, the crude TEA solution (740 g) was placed in another flask and given a thorough displacement with nitrogen gas. When it was subsequently heated and vacuumized and subjected to redistillation under the conditions of 160° C.–170° C./0.27–0.24 kPa, TEA having a purity of 99.3% was obtained in an amount of 380 g (yield 57.8%). Table 8 shows the conditions of the redistillation and the amounts of the fractions recovered. Table 9 shows the concentrations of the individual fractions and the amounts of the fractions recovered in the redistillation.

The TEA thus obtained was found to have a hue of no less than 10 and an absorbance determined by the phosphorus coloration test of 0.07, 0.02, and 0.01 at wavelengths respectively of 420, 510, and 530 nm. The sample had a colorless, transparent appearance free of suspended matter and a smell of slight fragrance and not of pungent odor.

Comparative Example I-1

A 400 g portion of the bottoms obtained in Example I-1 was placed in a 500 ml three-neck flask made of glass and furnished with a capillary tube and given therein thorough displacement with nitrogen gas. When it was subsequently heated and vacuumized and subjected to one-stage distillation under the conditions of 175° C.–177° C./0.27–0.24 kPa, TEA having a purity of 95.0% was obtained in an amount of 161 g (yield 40.2%). Table 10 shows the conditions for the one-stage distillation and the amounts of the fractions recovered. Table 11 shows the concentrations of the individual fractions and the amounts of the fractions recovered in the one-stage distillation.

The TEA thus obtained was found to have a hue of 80 and an absorbance determined by the phosphorus coloration test. of 1.2, 0.19, and 0.29 at wavelengths respectively of 420, 510, and 530 nm.

Comparative Example I-2

A 800 g portion of the bottoms obtained in Example I-2 was placed in a 1,000 ml three-neck flask made of glass and furnished with a capillary tube and given therein thorough displacement with nitrogen gas. When it was subsequently heated and vacuumized and subjected to one-stage distillation under the conditions of 168° C.–178° C./0.31–0.29 kPa, TEA having a purity of 98.5% was obtained in an amount of 358 g (yield 44.8%). Table 12 shows the conditions for the one-stage distillation and the amounts of the fractions recovered. Table 13 shows the concentrations of the individual fractions and the amounts of the fractions recovered in the one-stage distillation.

The TEA thus obtained was found to have a hue of 35 and an absorbance determined by the phosphorus coloration test of 0.13, 0.09, and 0.04 at wavelengths respectively of 420, 510, and 530 nm.

Comparative Example I-3

A 400 g portion of the bottoms obtained in Example I-1 was placed in a 500 ml three-neck flask made of glass and furnished with a capillary tube and given therein thorough displacement with nitrogen gas. When it was subsequently heated and vacuumized and subjected to one-stage distillation under the conditions of 186° C.–190° C./0.30–0.27 kPa, TEA having a purity of 93.0% was obtained in an amount of 151 g (yield 37.8%). The distilling column was packed with 10. cm of fillers (Dixon packing measuring 3 mm in outside diameter and made of SUS 316). Table 14 shows the conditions for the one-stage distillation (using fillers) and the amounts of the fractions recovered. Table 15 shows the concentrations of the individual fractions and the amounts of the fractions recovered in the one-stage distillation (using fillers).

The TEA thus obtained was found to have a hue of not less than 100 and an absorbance determined by the phosphorus coloration test of 1.8, 0.61, and 0.49 at wavelengths respectively of 420, 510, and 530 nm.

Table 1 shows the process of distillation and the discretion of distillation on account of use of fillers regarding Examples 1 and 2, and Comparative Examples 1–3.

TABLE 1

| (Condition of distillation in distilling column) | | |
|---|---|---|
| | Process | Filler |
| Example I-1 | Crude distillation | No |
| | Redistillation | No |
| Example I-2 | Crude distillation | No |
| | Redistillation | No |

TABLE 1-continued

(Condition of distillation in distilling column)

| | Process | Filler |
|---|---|---|
| Comparative Example I-1 | One-stage distillation | No |
| Comparative Example I-2 | One-stage distillation | No |
| Comparative Example I-3 | One-stage distillation | Yes |

Size of distilling column: Packed type, using common ground joints; Measuring 26 mm in inside diameter and 400 mm in bed length Filler: Dixon packing; Measuring 3.0 mm in outside diameter, using SUS 316 as material Packed bed length 100 mm

TABLE 2

Crude distillation of Example I-1: Raw material supplied 400 g

| Column top temperature (° C.) | Column bottom temperature (° C.) | Bath temperature (° C.) | Pressure (kPa) | | Amount recovered (g) | Recovery ratio of individual fraction (%) | Ratio of cumulative recovery (%) |
|---|---|---|---|---|---|---|---|
| 151 | 174 | 175.3 | 0.48 | Start of distillation | | | |
| 172 | 175 | 178.0 | 0.35 | OH-1 | 42.0 | 10.5 | 10.5 |
| 174 | 176 | 180.6 | 0.33 | OH-2 | 41.1 | 10.3 | 20.8 |
| 175 | 178 | 182.2 | 0.33 | OH-3 | 41.6 | 10.4 | 31.2 |
| 175 | 177 | 180.3 | 0.33 | OH-4 | 40.6 | 10.2 | 41.3 |
| 173 | 176 | 180.2 | 0.29 | OH-5 | 40.8 | 10.2 | 51.5 |
| 173 | 176 | 180.4 | 0.29 | OH-6 | 38.4 | 9.6 | 61.1 |
| 173 | 176 | 180.4 | 0.27 | OH-7 | 40.9 | 10.2 | 71.4 |
| 170 | 174 | 180.3 | 0.21 | OH-8 | 38.9 | 9.7 | 81.1 |
| 167 | 178 | 182.2 | 0.21 | OH-9 | 24.1 | 6.0 | 87.1 |
| 166 | 180 | 188.1 | 0.21 | OH-10 | 24.9 | 6.2 | 93.3 |

OH-1–9 were used as raw materials for redistillation.

TABLE 3

Concentration in crude distillation of Example I-1

| | | Concentration (wt %) | | | Weight (g) | | |
|---|---|---|---|---|---|---|---|
| Fraction | Ratio of recovery Cumulative | DEA | TEA | High-boiling substance | Amount recovered | DEA | TEA | High-boiling substance |
| OH-1 | 10.5 | 41.8 | 58.2 | 0.0 | 42.0 | 17.6 | 24.4 | 0.0 |
| OH-2 | 20.8 | 12.4 | 87.4 | 0.2 | 41.1 | 5.1 | 35.9 | 0.1 |
| OH-3 | 31.2 | 4.1 | 94.3 | 1.7 | 41.6 | 1.7 | 39.2 | 0.7 |
| OH-4 | 41.3 | 1.7 | 95.3 | 3.0 | 40.6 | 0.7 | 38.7 | 1.2 |
| OH-5 | 51.5 | 1.1 | 95.1 | 3.8 | 40.8 | 0.4 | 38.8 | 1.6 |
| OH-6 | 61.1 | 0.4 | 94.5 | 5.1 | 38.4 | 0.2 | 36.3 | 2.0 |
| OH-7 | 71.4 | 0.2 | 92.4 | 7.4 | 40.9 | 0.1 | 37.8 | 3.0 |
| OH-8 | 81.1 | 0.1 | 90.9 | 9.0 | 38.9 | 0.0 | 35.3 | 3.5 |
| OH-9 | 87.1 | 0.1 | 82.9 | 17.1 | 24.1 | 0.0 | 20.0 | 4.1 |

TABLE 4

Redistillation of Example I-1: Raw material supplied 345 g

| Column top temperature (° C.) | Column bottom temperature (° C.) | Bath temperature (° C.) | Pressure (kPa) | | Amount recovered (g) | Recovery ratio of individual fraction (%) | Ratio of cumulative recovery (%) |
|---|---|---|---|---|---|---|---|
| 136 | 163 | 170.6 | 0.25 | Start of distillation | | | |

TABLE 4-continued

Redistillation of Example I-1: Raw material supplied 345 g

| Column top temperature (° C.) | Column bottom temperature (° C.) | Bath temperature (° C.) | Pressure (kPa) | | Amount recovered (g) | Recovery ratio of individual fraction (%) | Ratio of cumulative recovery (%) |
|---|---|---|---|---|---|---|---|
| 160 | 164 | 168.5 | 0.25 | OH-1 | 34.2 | 9.9 | 9.9 |
| 162 | 166 | 172.0 | 0.25 | OH-2 | 35.6 | 10.3 | 20.2 |
| 163 | 168 | 173.2 | 0.25 | OH-3 | 36.8 | 10.7 | 30.9 |
| 164 | 169 | 176.3 | 0.25 | OH-4 | 41.0 | 11.9 | 42.8 |
| 164 | 168 | 177.2 | 0.25 | OH-5 | 43.1 | 12.5 | 55.3 |
| 164 | 169 | 178.0 | 0.25 | OH-6 | 32.2 | 9.3 | 64.6 |
| 165 | 169 | 178.8 | 0.25 | OH-7 | 34.1 | 9.9 | 74.5 |
| 166 | 171 | 180.4 | 0.25 | OH-8 | 36.8 | 10.7 | 85.2 |
| 168 | 172 | 184.0 | 0.25 | OH-9 | 32.2 | 9.3 | 94.5 |
| 148 | 173 | 183.9 | 0.25 | OH-10 | 4.7 | 1.4 | 95.9 |

OH-1–3: High DEA concentrations.
OH-4–8: Obtained in the form of TEA of a purity of 99%.
OH-9–10: High-boiling compounds of high concentrations.

TABLE 5

Concentration in redistillation of Example I-1

| | | Concentration (wt %) | | | Weight (g) | | | |
|---|---|---|---|---|---|---|---|---|
| Fraction | Ratio of recovery Cumulative | DEA | TEA | High-boiling substance | Amount recovered | DEA | TEA | High-boiling substance |
| OH-1 | 9.9 | 46.5 | 53.5 | 0.0 | 34.2 | 15.9 | 18.3 | 0.0 |
| OH-2 | 20.2 | 17.9 | 82.1 | 0.0 | 35.6 | 6.4 | 29.2 | 0.0 |
| OH-3 | 30.9 | 0.8 | 99.1 | 0.1 | 36.8 | 0.3 | 36.5 | 0.0 |
| OH-4 | 42.8 | 0.2 | 99.5 | 0.3 | 41.0 | 0.1 | 40.8 | 0.1 |
| OH-5 | 55.3 | 0.1 | 99.4 | 0.6 | 43.1 | 0.0 | 42.8 | 0.2 |
| OH-6 | 64.6 | 0.0 | 99.1 | 0.9 | 32.2 | 0.0 | 31.9 | 0.3 |
| OH-7 | 74.5 | 0.0 | 98.8 | 1.2 | 34.1 | 0.0 | 33.7 | 0.4 |
| OH-8 | 85.2 | 0.0 | 98.2 | 1.8 | 36.8 | 0.0 | 36.1 | 0.7 |
| OH-9 | 94.5 | 0.0 | 86.0 | 14.0 | 32.2 | 0.0 | 27.7 | 4.5 |
| OH-10 | 95.9 | 0.0 | 67.1 | 32.9 | 4.7 | 0.0 | 3.2 | 1.5 |

TABLE 6

Crude distillation of Example I-2: Raw material supplied 800 g

| Column top temperature (° C.) | Column bottom temperature (° C.) | Bath temperature (° C.) | Pressure (kPa) | | Amount recovered (g) | Recovery ratio of individual fraction (%) | Ratio of cumulative recovery (%) |
|---|---|---|---|---|---|---|---|
| 139 | 164 | 174.6 | 0.37 | Start of distillation | | | |
| 140 | 168 | 180.1 | 0.33 | OH-1 | 90.3 | 11.3 | 11.3 |
| 160 | 169 | 181.5 | 0.33 | OH-2 | 88.3 | 11.0 | 22.3 |
| 160 | 172 | 183.1 | 0.33 | OH-3 | 89.9 | 11.2 | 33.6 |
| 161 | 171 | 182.5 | 0.33 | OH-4 | 84.2 | 10.5 | 44.1 |
| 162 | 172 | 183.1 | 0.33 | OH-5 | 86.6 | 10.8 | 54.9 |
| 162 | 174 | 184.5 | 0.33 | OH-6 | 98.9 | 12.4 | 67.3 |
| 162 | 177 | 184.6 | 0.33 | OH-7 | 86.2 | 10.8 | 78.1 |
| 163 | 179 | 185.5 | 0.31 | OH-8 | 85.2 | 10.6 | 88.7 |
| 165 | 180 | 187.3 | 0.31 | OH-9 | 35.4 | 4.4 | 93.1 |
| 182 | 183 | 195.3 | 0.31 | OH-10 | 18.0 | 2.3 | 95.4 |

OH-1–9 were used as raw materials for redistillation.

TABLE 7

Concentration in crude distillation of Example I-2

| | Concentration (wt %) | | | | Weight (g) | | | |
|---|---|---|---|---|---|---|---|---|
| Fraction | Ratio of recovery Cumulative | DEA | TEA | High-boiling substance | Amount recovered | DEA | TEA | High-boiling substance |
| OH-1 | 11.3 | 66.3 | 33.7 | 0.0 | 90.3 | 59.9 | 30.4 | 0.0 |
| OH-2 | 22.3 | 12.4 | 87.6 | 0.0 | 88.3 | 10.9 | 77.3 | 0.0 |
| OH-3 | 33.6 | 0.6 | 99.3 | 0.1 | 89.9 | 0.6 | 89.3 | 0.1 |
| OH-4 | 44.1 | 0.2 | 99.5 | 0.3 | 84.2 | 0.2 | 83.8 | 0.2 |
| OH-5 | 54.9 | 0.1 | 99.4 | 0.5 | 86.6 | 0.1 | 86.1 | 0.4 |
| OH-6 | 67.3 | 0.0 | 99.2 | 0.8 | 98.9 | 0.0 | 98.2 | 0.8 |
| OH-7 | 78.1 | 0.0 | 98.7 | 1.3 | 86.2 | 0.0 | 85.1 | 1.1 |
| OH-8 | 88.7 | 0.0 | 97.5 | 2.5 | 85.2 | 0.0 | 83.1 | 2.1 |
| OH-9 | 93.1 | 0.0 | 96.3 | 3.7 | 35.4 | 0.0 | 34.0 | 1.3 |
| OH-10 | 95.4 | 0.0 | 86.5 | 13.6 | 18.0 | 0.0 | 15.6 | 2.4 |

TABLE 8

Redistillation of Example I-2: Raw material supplied 740 g

| Column top temperature (° C.) | Column bottom temperature (° C.) | Bath temperature (° C.) | Pressure (kPa) | | Amount recovered (g) | Recovery ratio of individual fraction (%) | Ratio of cumulative recovery (%) |
|---|---|---|---|---|---|---|---|
| 144 | 164 | 169.3 | 0.40 | Start of distillation | | | |
| 153 | 163 | 170.8 | 0.27 | OH-1 | 77.7 | 10.5 | 10.5 |
| 154 | 162 | 171.3 | 0.27 | OH-2 | 77.9 | 10.5 | 21.0 |
| 154 | 164 | 171.8 | 0.27 | OH-3 | 75.6 | 10.2 | 31.2 |
| 152 | 162 | 171.5 | 0.27 | OH-4 | 80.6 | 10.9 | 42.1 |
| 152 | 160 | 171.5 | 0.27 | OH-5 | 73.7 | 10.0 | 52.1 |
| 151 | 160 | 171.5 | 0.27 | OH-6 | 73.9 | 10.0 | 62.1 |
| 151 | 160 | 171.6 | 0.27 | OH-7 | 71.7 | 9.7 | 71.8 |
| 151 | 160 | 171.8 | 0.27 | OH-8 | 79.9 | 10.8 | 82.6 |
| 151 | 160 | 172.4 | 0.27 | OH-9 | 48.1 | 6.5 | 89.1 |
| 151 | 162 | 172.7 | 0.27 | OH-10 | 35.6 | 4.9 | 93.9 |
| 149 | 162 | 172.7 | 0.24 | OH-11 | 9.9 | 1.3 | 95.2 |

OH-1–3: High DEA concentrations.
OH-4–8: Obtained in the form of TEA having a purity of 99%.
OH-9–11: High-boiling substances of high concentrations.

TABLE 9

Concentration in redistillation of Example I-2

| | Concentration (wt %) | | | | Weight (g) | | | |
|---|---|---|---|---|---|---|---|---|
| Fraction | Ratio of recovery Cumulative | DEA | TEA | High-boiling substance | Amount recovered | DEA | TEA | High-boiling substance |
| OH-1 | 10.5 | 55.8 | 44.2 | 0.0 | 77.7 | 43.4 | 34.3 | 0.0 |
| OH-2 | 21.0 | 9.3 | 90.6 | 0.1 | 77.9 | 7.2 | 70.6 | 0.1 |
| OH-3 | 31.2 | 0.9 | 98.9 | 0.2 | 75.6 | 0.7 | 74.7 | 0.2 |
| OH-4 | 42.1 | 0.4 | 99.4 | 0.3 | 80.6 | 0.3 | 80.1 | 0.2 |
| OH-5 | 52.1 | 0.2 | 99.5 | 0.4 | 73.7 | 0.1 | 73.3 | 0.3 |
| OH-6 | 62.1 | 0.0 | 99.5 | 0.5 | 73.9 | 0.0 | 73.5 | 0.4 |
| OH-7 | 71.8 | 0.0 | 99.2 | 0.8 | 71.7 | 0.0 | 71.1 | 0.6 |
| OH-8 | 82.6 | 0.0 | 98.9 | 1.1 | 79.9 | 0.0 | 79.0 | 0.9 |
| OH-9 | 89.1 | 0.0 | 98.7 | 1.3 | 48.1 | 0.0 | 47.5 | 0.6 |
| OH-10 | 93.9 | 0.0 | 98.0 | 2.0 | 35.9 | 0.0 | 35.2 | 0.7 |

TABLE 10

One-stage distillation of Comparative Example I-1: Raw material supplied 400 g

| Column top temperature (° C.) | Column bottom temperature (° C.) | Bath temperature (° C.) | Pressure (kPa) | | Amount recovered (g) | Recovery ratio of individual fraction (%) | Ratio of cumulative recovery (%) |
|---|---|---|---|---|---|---|---|
| 155 | 176 | 178.3 | 0.33 | Start of distillation | | | |
| 172 | 175 | 178.0 | 0.27 | OH-1 | 41.3 | 10.3 | 10.3 |
| 174 | 176 | 178.5 | 0.27 | OH-2 | 41.8 | 10.5 | 20.8 |
| 175 | 175 | 179.8 | 0.27 | OH-3 | 40.9 | 10.2 | 31.0 |
| 175 | 175 | 180.3 | 0.27 | OH-4 | 40.2 | 10.1 | 41.1 |
| 173 | 176 | 180.2 | 0.27 | OH-5 | 40.8 | 10.2 | 51.3 |
| 172 | 176 | 180.4 | 0.25 | OH-6 | 39.9 | 10.0 | 61.2 |
| 173 | 177 | 180.4 | 0.24 | OH-7 | 40.1 | 10.0 | 71.3 |
| 174 | 178 | 180.3 | 0.24 | OH-8 | 39.9 | 10.0 | 81.2 |
| 176 | 180 | 182.2 | 0.24 | OH-9 | 30.1 | 7.5 | 88.8 |
| 178 | 185 | 187.1 | 0.24 | OH-10 | 18.9 | 4.7 | 93.5 |

OH-4–7 were obtained in the form of TEA having a purity of 95%.

TABLE 11

Concentration in one-stage distillation of Comparative Example I-1

| | | Concentration (wt %) | | | Weight (g) | | | |
|---|---|---|---|---|---|---|---|---|
| Fraction | Ratio of recovery Cumulative | DEA | TEA | High-boiling substance | Amount recovered | DEA | TEA | High-boiling substance |
| OH-1 | 10.3 | 43.3 | 56.8 | 0.0 | 41.3 | 17.9 | 23.4 | 0.0 |
| OH-2 | 20.8 | 11.4 | 88.4 | 0.2 | 41.8 | 4.8 | 37.0 | 0.1 |
| OH-3 | 31.0 | 4.1 | 94.6 | 1.3 | 40.9 | 1.7 | 38.7 | 0.5 |
| OH-4 | 41.1 | 1.8 | 95.5 | 2.8 | 40.2 | 0.7 | 38.4 | 1.1 |
| OH-5 | 51.3 | 0.8 | 95.7 | 3.5 | 40.8 | 0.3 | 39.0 | 1.4 |
| 0H-6 | 61.2 | 0.2 | 95.0 | 4.8 | 39.9 | 0.1 | 37.9 | 1.9 |
| OH-7 | 71.3 | 0.0 | 94.1 | 5.9 | 40.1 | 0.0 | 37.7 | 2.4 |
| OH-8 | 81.2 | 0.0 | 92.9 | 7.1 | 39.9 | 0.0 | 37.1 | 2.8 |
| OH-9 | 88.8 | 0.0 | 81.9 | 18.2 | 30.1 | 0.0 | 24.6 | 5.5 |
| OH-10 | 93.5 | 0.0 | 60.0 | 40.0 | 18.9 | 0.0 | 11.3 | 7.6 |

TABLE 12

One-stage distillation of Comparative Example I-2: Raw material supplied 800 g

| Column top temperature (° C.) | Column bottom temperature (° C.) | Bath temperature (° C.) | Pressure (kPa) | | Amount recovered (g) | Recovery ratio of individual fraction (%) | Ratio of cumulative recovery (%) |
|---|---|---|---|---|---|---|---|
| 139 | 164 | 174.6 | 0.37 | Start of distillation | | | |
| 162 | 168 | 170.8 | 0.31 | OH-1 | 79.2 | 9.9 | 9.9 |
| 162 | 169 | 177.6 | 0.31 | OH-2 | 90.1 | 11.3 | 21.2 |
| 162 | 171 | 183.1 | 0.31 | OH-3 | 92.0 | 11.5 | 32.7 |
| 163 | 172 | 183.4 | 0.31 | OH-4 | 80.2 | 10.0 | 42.7 |
| 162 | 172 | 182.6 | 0.31 | OH-5 | 89.4 | 11.2 | 53.9 |
| 162 | 173 | 183.4 | 0.31 | OH-6 | 98.9 | 12.4 | 66.2 |
| 163 | 174 | 184.8 | 0.31 | OH-7 | 89.2 | 11.2 | 77.4 |
| 162 | 174 | 184.2 | 0.29 | OH-8 | 76.5 | 9.6 | 86.9 |
| 160 | 178 | 190.0 | 0.29 | OH-9 | 45.2 | 5.7 | 92.6 |
| 182 | 183 | 195.3 | 0.27 | OH-10 | 16.0 | 2.0 | 94.6 |

OH-4–7 were obtained in the form of TEA having a purity of 98.5%.

TABLE 13

Concentration in one-stage distillation of Comparative Example I-2

| | | Concentration (wt %) | | | Weight (g) | | |
|---|---|---|---|---|---|---|---|
| Fraction | Ratio of recovery Cumulative | DEA | TEA | High-boiling substance | Amount recovered | DEA | TEA | High-boiling substance |
| OH-1 | 9.9 | 68.3 | 31.7 | 0.0 | 79.2 | 54.1 | 25.1 | 0.0 |
| OH-2 | 21.2 | 24.8 | 75.1 | 0.1 | 90.1 | 22.3 | 67.7 | 0.1 |
| OH-3 | 32.7 | 3.2 | 96.6 | 0.2 | 92.0 | 2.9 | 88.9 | 0.2 |
| OH-4 | 42.7 | 1.5 | 98.0 | 0.5 | 80.2 | 1.2 | 78.6 | 0.4 |
| OH-5 | 53.9 | 0.5 | 98.8 | 0.7 | 89.4 | 0.5 | 88.3 | 0.7 |
| OH-6 | 66.2 | 0.1 | 98.8 | 1.1 | 98.9 | 0.1 | 97.7 | 1.0 |
| OH-7 | 77.4 | 0.0 | 98.5 | 1.5 | 89.2 | 0.0 | 87.9 | 1.3 |
| OH-8 | 86.9 | 0.0 | 97.7 | 2.3 | 76.5 | 0.0 | 74.7 | 1.8 |
| OH-9 | 92.6 | 0.0 | 96.1 | 3.9 | 45.2 | 0.0 | 43.4 | 1.8 |
| OH-10 | 94.6 | 0.0 | 85.3 | 14.7 | 16.0 | 0.0 | 13.7 | 2.3 |

TABLE 14

One-stage distillation (using fillers) of Comparative Example I-3:
Raw material supplied 400 g

| Column top temperature (° C.) | Column bottom temperature (° C.) | Bath temperature (° C.) | Pressure (kPa) | | Amount recovered (g) | Recovery ratio of individual fraction (%) | Ratio of cumulative recovery (%) |
|---|---|---|---|---|---|---|---|
| 175 | 184 | 188.4 | 0.32 | Start of distillation | | | |
| 184 | 186 | 188.3 | 0.29 | OH-1 | 40.3 | 10.1 | 10.1 |
| 185 | 187 | 188.8 | 0.29 | OH-2 | 42.4 | 10.6 | 20.7 |
| 184 | 186 | 188.9 | 0.29 | OH-3 | 41.1 | 10.3 | 31.0 |
| 185 | 187 | 190.4 | 0.29 | OH-4 | 40.5 | 10.1 | 41.1 |
| 185 | 187 | 190.9 | 0.29 | OH-5 | 40.4 | 10.1 | 51.2 |
| 184 | 187 | 190.4 | 0.28 | OH-6 | 40.2 | 10.1 | 61.2 |
| 184 | 188 | 190.7 | 0.27 | OH-7 | 39.9 | 10.0 | 71.2 |
| 183 | 189 | 190.9 | 0.27 | OH-8 | 41.1 | 10.3 | 81.5 |
| 185 | 190 | 192.5 | 0.27 | OH-9 | 29.8 | 7.5 | 88.9 |
| 188 | 195 | 198.9 | 0.27 | OH-10 | 19.5 | 4.9 | 93.8 |

OH-3–6 were obtained as TEA having a purity of 93%.

TABLE 15

Concentration in one-stage distillation of Comparative Example I-3

| | | Concentration (wt %) | | | Weight (g) | | |
|---|---|---|---|---|---|---|---|
| Fraction | Ratio of recovery Cumulative | DEA | TEA | High-boiling substance | Amount recovered | DEA | TEA | High-boiling substance |
| OH-1 | 10.1 | 41.8 | 58.2 | 0.0 | 40.3 | 16.8 | 23.5 | 0.0 |
| OH-2 | 20.7 | 9.3 | 88.2 | 2.4 | 42.4 | 4.0 | 37.4 | 1.0 |
| OH-3 | 31.0 | 4.2 | 92.4 | 3.4 | 41.1 | 1.7 | 38.0 | 1.4 |
| OH-4 | 41.1 | 2.1 | 93.8 | 4.1 | 40.5 | 0.8 | 38.0 | 1.7 |
| OH-5 | 51.2 | 1.1 | 93.7 | 5.2 | 40.4 | 0.4 | 37.9 | 2.1 |
| OH-6 | 61.2 | 0.4 | 93.2 | 6.4 | 40.2 | 0.2 | 37.5 | 2.6 |
| OH-7 | 71.2 | 0.2 | 91.2 | 8.5 | 39.9 | 0.1 | 36.4 | 3.4 |
| OH-8 | 81.5 | 0.1 | 89.2 | 10.7 | 41.1 | 0.0 | 36.7 | 4.4 |
| OH-9 | 88.9 | 0.0 | 81.3 | 18.7 | 29.8 | 0.0 | 24.2 | 5.6 |
| OH-10 | 93.8 | 0.0 | 61.2 | 38.8 | 19.5 | 0.0 | 11.9 | 7.6 |

(Size of Distilling column): Examples II-1–8 and Comparative examples II-1–3

Packed type, using common ground joints.
Measuring 26 mm in inside diameter and 400 mm in length No filler used.

Example II-1

In a plant for producing ethanolamine, the catalyst process was implemented by continuously introducing EO, liquid ammonia, and MEA into a-reactor packed with a catalyst at such flow rates as to enable their concentrations to reach 18.1, 70.9, and 11.0% by weight respectively. The reaction was performed adiabatically at a reaction pressure of 10 MPa, at an inlet temperature of 45° C. and at a LHSV of 5.9. The catalyst used was a ZSM-5 type zeolite which had undergone ion exchange with lanthanum. The aqueous ammonia process was implemented by continuously introducing EO and an aqueous 37% ammonia solution into another reactor at such flow rates as to enable the molar ratio of EO and ammonia to reach 0.28. The degree of conversion of EO at the plant for the production of ethanolamine by the catalyst process and the aqueous ammonia process was nearly 100%. The reaction solution consequently obtained was deprived of the unaltered ammonia of the catalyst process by the pressure distillation. The remaining solution and the reaction solution of the aqueous ammonia process were mixed together. The mixing ratio (weight) of catalyst process/aqueous ammonia process was 60/40.

Figure 4:
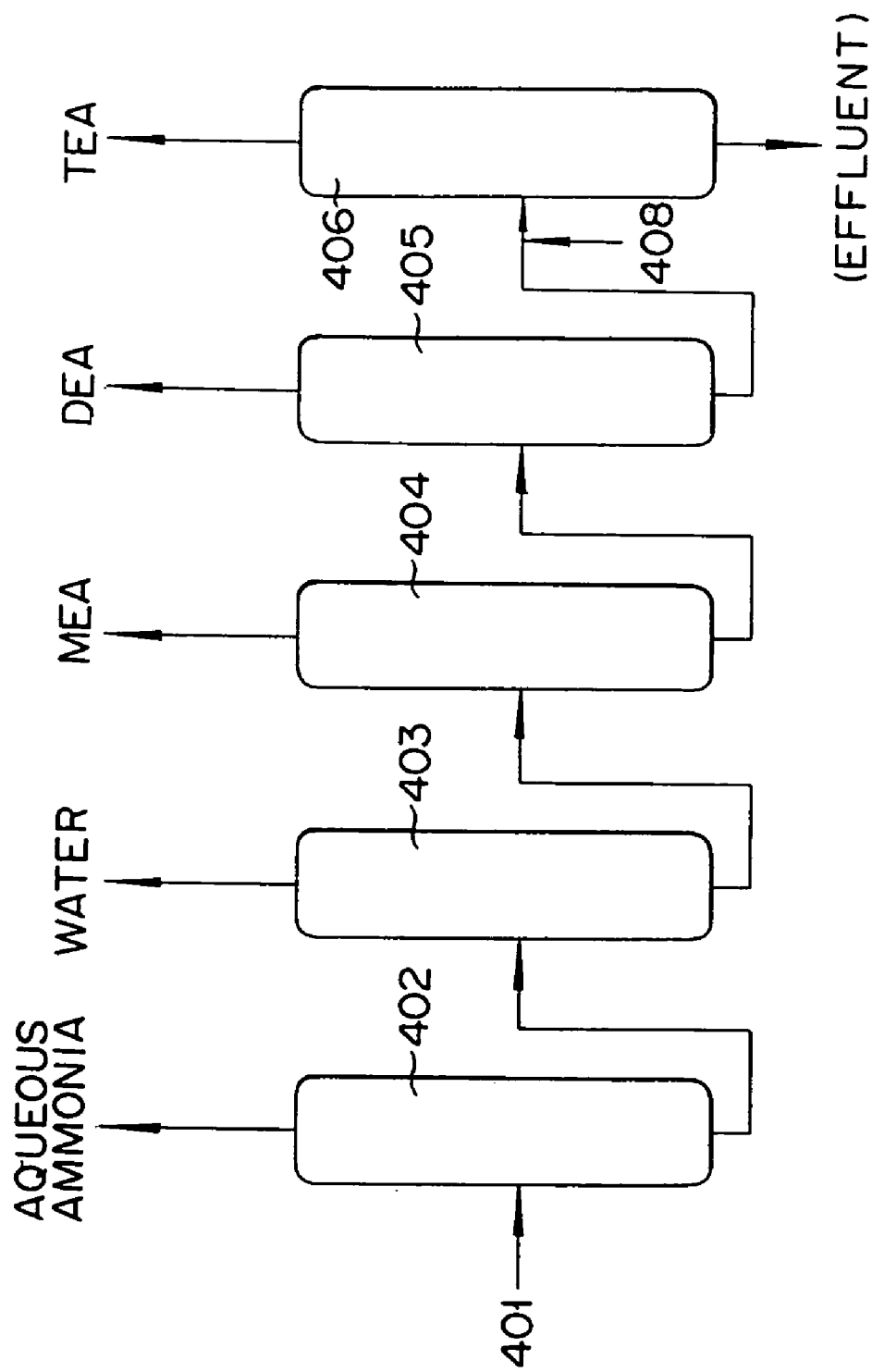
FIG. 4 is a diagram schematically illustrating a flow of the distillation of the reaction solution.

FIG. 4 is a diagram schematically illustrating a flow of the operation of distilling the reaction solution. In FIG. 4, a reaction solution 401 (a mixture of the solutions of the catalyst and aqueous ammonia processes) was first distilled continuously in an ammonia stripping column 402 to distill aqueous ammonia, then continuously distilled in a dehydrating column 403 to distill water, continuously distilled in a MEA rectifying column 404 to distill MEA, and further distilled continuously in a DEA rectifying column 405 to distill DEA and obtain the raw material TEA in the form of bottoms. The bottoms had a composition formed of 91.7% by weight of TEA, 7.6% by weight of DEA, and 0.7% by weight of high-boiling compounds.

In FIG. 4, the raw material TEA and a low-boiling compound 408 were mixed together and fed to a TEA rectifying column 406, batch distillation, to distill TEA. Specifically, a 500 g portion of the bottom (raw material TEA) and 15 g of distilled water were mixed together and the resultant mixture was placed in a 600 ml three-neck flask made of glass and furnished with a capillary tube and given therein thorough displacement with nitrogen gas. Thereafter, the resultant mixture was heated and vacuumized, treated under the conditions of 90° C.–170° C./400–10 hPa to expel water, and thereafter distilled under the conditions of 160° C.–167° C. Consequently, TEA having a purity of 99.7% by weight was obtained in an amount of 300 g (yield 59.9%). Incidentally, the distillation was performed by introducing a forced current of nitrogen gas via the capillary tube into the reactor. The refined TEA obtained consequently was tested for APHA. The results are shown in Table 16.

The absorbance of the resultant TEA determined by the phosphorus coloration test was 0.09, 0.03, and 0.03 at wavelengths of 420, 510, and 530 nm respectively. The sample had a colorless transparent appearance free of suspended matter and a small of slight fragrance and not of pungent odor. The aging test showed a change of APHA from 20 to 25.

Comparative Example II-1

TEA was obtained by following the procedure of Example II-1 while omitting the addition of water to the raw material TEA. The TEA thus obtained was tested for APHA. The results are shown in Table 16.

The absorbance of the refined TEA as determined by the phosphorus coloration test was 0.66, 0.20, and 0.13 at wavelengths of 420, 510, and 530 nm respectively. The sample has a colorless transparent appearance free of suspended matter and a small of slight fragrance and not of pungent odor.

TABLE 16

| | | Recovery ratio of TEA (%), purity (%), and value of APHA | | | | | | | | |
|---|---|---|---|---|---|---|---|---|---|---|
| Example II-1 | Recovery ratio | 10.26 | 21.48 | 31.19 | 41.12 | 50.77 | 61.68 | 71.29 | 81.38 | 91.09 |
| | Purity | 43.8 | 88.4 | 98.5 | 99.5 | 99.7 | 99.7 | 99.7 | 99.7 | 99.7 |
| | APHA | 35 | 50 | 50 | 40 | 20 | 20 | 20 | 20 | 25 |
| Comparative Example II-1 | Recovery ratio | 10.33 | 21.04 | 31.19 | 41.95 | 51.67 | 61.78 | 71.28 | 81.46 | 92.61 |
| | Purity | 38.5 | 87.9 | 98.6 | 99.5 | 99.7 | 99.8 | 99.8 | 99.7 | 99.6 |
| | APHA | 55 | 55 | 85 | 85 | 85 | 85 | 80 | 85 | 95 |

It is clear from Table 16 that Example II-1 decisively excels Comparative Example II-1 in APHA. To be specific, the average value of APHA at TEA purities exceeding 99% was 24.1 for Example II-1, for Comparative Example II-1 was 86.0, indicating that the ratio of (Example II-1)/(Comparative example II-1) was 0.28. Thus, Example II-1 brought an improvement of 72% in APHA, as compared with Comparative Example II-1.

When Example II-1 and Comparative Example II-1 are compared in the absorbance determined by the phosphorus coloration test, the TEA of Example II-1 excelled at all the wavelengths used in the test.

Example II-2

TEA was obtained by following the procedure of Example II-1 while adding 2.5 g of distilled water to the raw material TEA. The TEA consequently obtained was tested for APHA. The results are shown in Table 17.

The refined TEA was found to have a purity of 99.7% by weight was obtained in an amount of 304 g (yield 60.9%), and an average APHA of 28.3. The absorbance determined by the phosphorus coloration test was 0.11, 0.04, and 0.05 at wavelengths of 420, 510, and 530 nm, respectively. The sample had a colorless, transparent appearance free of suspended matter and a smell of slight fragrance and not of pungent odor. The aging test showed a change of the APHA from 23 to 30.

Example II-3

TEA was obtained by following the procedure of Example II-1 while adding 100 g of distilled water to the raw material TEA. The refined TEA consequently obtained was tested for APHA. The results are shown in Table 17.

TABLE 17

| Example | | Recovery ratio of TEA (%), purity (%), and value of APHA | | | | | | | |
|---|---|---|---|---|---|---|---|---|---|
| II-2 | Recovery ratio | 9.94 | 20.56 | 31.75 | 40.19 | 50.85 | 61.34 | 72.04 | 82.05 | 92.61 |
| | Purity | 39.4 | 81.8 | 98.7 | 99.6 | 99.7 | 99.8 | 99.8 | 99.8 | 99.6 |
| | APHA | 40 | 50 | 80 | 55 | 30 | 25 | 20 | 20 | 25 |
| II-1 | Recovery ratio | 10.26 | 21.48 | 31.19 | 41.12 | 50.77 | 61.68 | 71.29 | 81.38 | 91.09 |
| | Purity | 43.8 | 88.4 | 98.5 | 99.5 | 99.7 | 99.7 | 99.7 | 99.7 | 99.7 |
| | APHA | 35 | 50 | 50 | 40 | 20 | 20 | 20 | 20 | 25 |
| II-3 | Recovery ratio | 10.16 | 20.39 | 30.39 | 41.55 | 52.06 | 62.12 | 72.82 | 82.29 | 92.02 |
| | Purity | 39.2 | 88.1 | 98.3 | 99.5 | 99.8 | 99.8 | 99.8 | 99.7 | 99.5 |
| | APHA | 55 | 50 | 40 | 30 | 15 | 15 | 15 | 15 | 30 |

It is clear from Table 17 that the APHA hue was improved proportionally with the amount of distilled water added.

Example II-4

Figure 5:
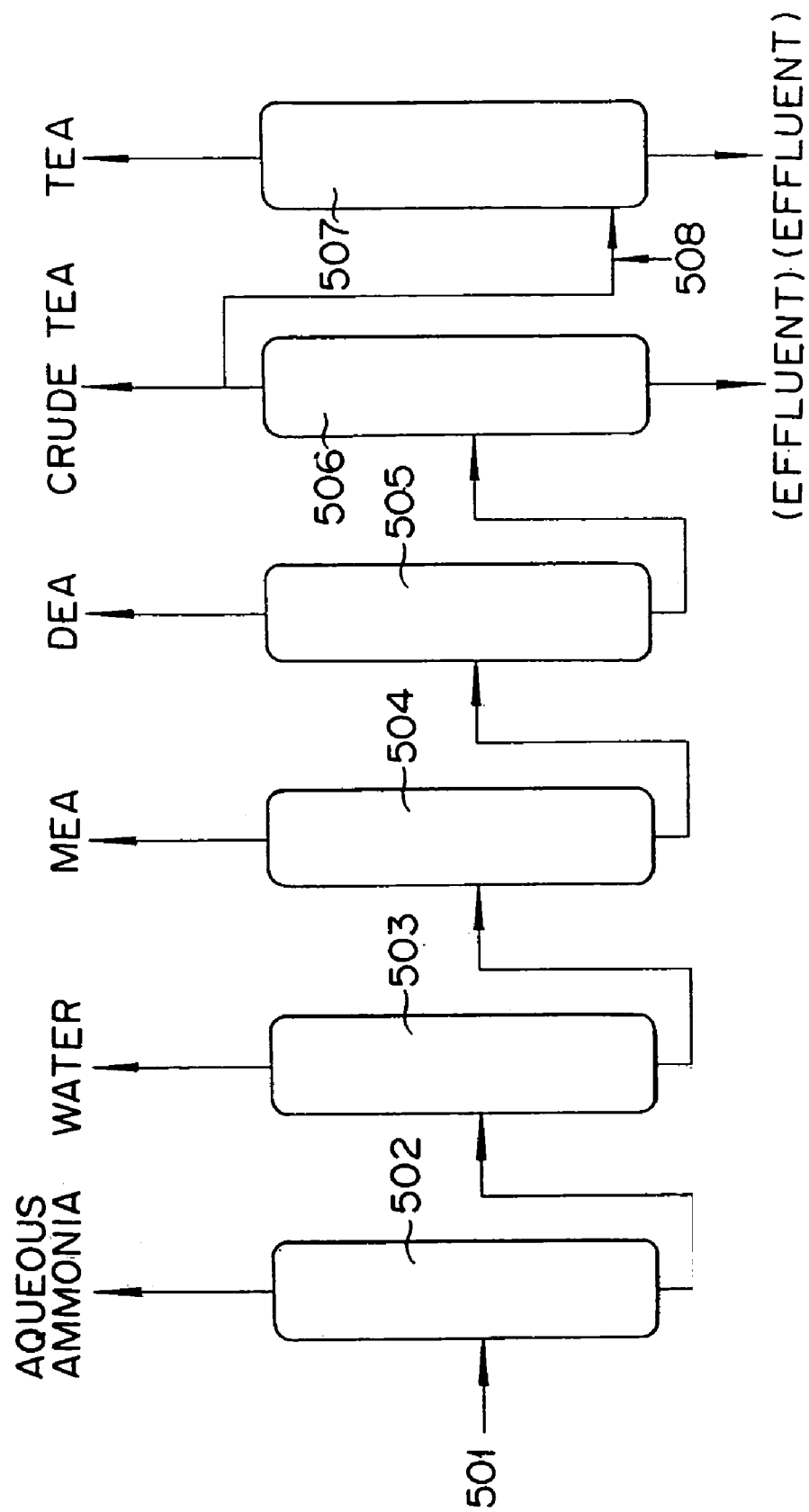
FIG. 5 is a diagram schematically illustrating another flow of the distillation of the reaction solution.

FIG. 5 is a diagram schematically illustrating a flow of the operation of distilling a reaction solution. In FIG. 5, a reaction solution 501 (a mixture of the solutions of the catalyst and aqueous ammonia processes) was first continuously distilled in an ammonia stripping column 502 to distill aqueous ammonia, then continuously distilled in a dehydrating column 503 to distill water, continuously distilled in a MEA rectifying-column 504 to distill MEA, and further continuously distilled in a DEA rectifying column 505 to distill DEA and obtain the raw material TEA in the form of bottoms. The raw material TEA was continuously distilled in a TEA distilling column 506 to distill crude TEA. The bottoms had a composition formed of 95% by weight of TEA, 4.9% by weight of DEA, and 0.1% by weight of a high-boiling compound.

Further, the crude TEA-and a low-boiling mixture 508 were mixed together and subjected to batch distillation in a TEA rectifying column 507 to distill refined TEA. Specifically, a 500 g portion of the bottoms (crude TEA) and 15 g of distilled water were mixed together. The resultant mixture was placed in a 500 ml three-neck flask made of glass and furnished with a capillary tube and given there in thorough displacement with nitrogen gas. It was subsequently heated and vacuumized, treated under the conditions of 90° C.–170° C./400–10 hPa to expel water, and distilled under the conditions of 173° C.–175° C./6.6–3.0 hPa. Consequently, TEA having a purity of 99.7% by weight was obtained in an amount of 372 g (yield 74.4%). The refined TEA thus obtained was tested for APHA. The results are shown in Table 18.

The absorbance of the refined TEA determined by the phosphorus coloration test was 0.08, 0.03, and 0.02 at wavelengths of 420, 510, and 530 nm, respectively. The sample had a colorless, transparent appearance free of suspended matter and a smell of slight fragrance and not of pungent odor. The aging test showed a change of the APHA from 10 to 15.

Comparative Example II-2

Refined TEA was obtained by following the procedure of Example II-4 without the addition of water for the raw material TEA solution for rectification. The refined TEA thus obtained was tested for APHA. The results are shown in Table 18.

The absorbance of the refined TEA determined by the phosphorus coloration test was 0.09, 0.04, and 0.02 at wavelengths of 420, 510, and 530 nm, respectively. The sample had a colorless, transparent appearance free of suspended matter and a smell of slight fragrance and not of pungent odor. The aging test showed a change of APH from-15 to 25.

The refined TEA was found to have a purity of 99.7% by weight was obtained in an amount of 308 g (yield 61.6%), and an average APHA of 20.0 The absorbance determined by the phosphorus coloration test was 0.07, 0.02, and 0.02 at wavelengths of 420, 510, and 530 nm, respectively. The sample had a colorless, transparent appearance free of suspended matter and a smell of slight fragrance and not of pungent odor. The aging test showed a change of the APHA from 18 to 22.

TABLE 18

| | | Recovery ratio of TEA (%), purity (%), and value of APHA | | | | | | | | |
|---|---|---|---|---|---|---|---|---|---|---|
| Example II-4 | Recovery ratio | 10.19 | 20.58 | 31.84 | 45.00 | 55.47 | — | 73.68 | 85.77 | 94.98 |
| | Purity | 59.0 | 94.5 | 99.2 | 99.7 | 99.8 | — | 99.8 | 99.7 | 99.7 |
| | APHA | 30 | 8 | 5 | 7 | 7 | — | 10 | 17 | 22 |

TABLE 18-continued

Recovery ratio of TEA (%), purity (%), and value of APHA

| Comparative Example II-2 | Recovery ratio | 10.12 | 21.52 | 21.11 | 42.26 | 53.59 | 64.46 | 77.57 | 88.87 | 97.52 |
|---|---|---|---|---|---|---|---|---|---|---|
| | Purity | 57 | 94.6 | 99.5 | 99.7 | 99.8 | 99.8 | 99.8 | 99.8 | 99.8 |
| | APHA | 25 | 20 | 8 | 15 | 13 | 13 | 15 | 17 | 33 |

It is clear from Table 18 that Example II-4 excelled Comparative Example II-2. Specifically, the average APHA at TEA purities exceeding 99% was 10.9 for Example II-4, and. 15.9 for Comparative Example II-2, indicating the ratio of (Example II-4)/(Comparative Example II-2) was 0.69. Thus, Example II-4 brought an improvement of 31% inAPHV, as compared with Comparative Example II-2.

Also in the phosphorus coloration test, the TEA of Example II-4 excelled that of Comparative Example II-2 at wavelengths of 420 and 510 nm. Further in the aging test of APHA, the TEA of Example II-4 showed a smaller change than that of Comparative Example II-2.

Examples II-5, 6, 7, and 8 and Comparative Example II-3

Refined TEA was obtained by following the procedure of Example II-1 with the addition of 3% by weight of MEA (Example II-5), the addition of 3% by weight of water +1% by weight of MEA (Example II-6), the addition of 3% by weight of distilled water (Example II-7), the addition of 3% by weight of ethanol (Example II-8), and without the addition of water (Comparative Example II-3) to the raw material TEA solution for rectification. These products of TEA were tested for APHA. The results are shown in Table 19.

TABLE 19

Recovery ratio of TEA (%), purity (%), and value of APHA

| Example II-5 | Recovery ratio | 10.4 | 20.3 | 31.0 | 41.4 | 51.0 | 60.8 | 69.9 | 79.9 | 89.5 | 93.6 |
| | Purity | 49.4 | 90.6 | 98.4 | 99.7 | 99.7 | 99.8 | 99.8 | 99.8 | 99.8 | 99.7 |
| | APHA | 45 | 25 | 15 | 15 | 10 | 15 | 10 | 15 | 25 | 30 |
| Example II-6 | Recovery ratio | 10.5 | 21.1 | 30.5 | 40.5 | 50.5 | 60.6 | 70.7 | 79.7 | 89.0 | 91.8 |
| | Purity | 49.8 | 92.0 | 98.7 | 99.6 | 99.7 | 99.7 | 99.8 | 99.8 | 99.8 | 99.7 |
| | APHA | 95 | 12 | 12 | 10 | 10 | 10 | 10 | 12 | 17 | 25 |
| Example II-7 | Recovery ratio | 10.7 | 21.1 | 31.5 | 42.2 | 52.5 | 63.2 | 73.3 | 83.9 | 84.0 | 87.5 |
| | Purity | 51.2 | 88.2 | 98.8 | 99.7 | 99.7 | 99.8 | 99.8 | 99.8 | 99.8 | 99.1 |
| | APHA | 120 | 17 | 15 | 12 | 15 | 15 | 15 | 15 | 22 | 30 |
| Example II-8 | Recovery ratio | 10.8 | 21.0 | 31.2 | 41.8 | 52.3 | 63.0 | 72.8 | 83.3 | 91.0 | 94.9 |
| | Purity | 51.3 | 87.0 | 98.4 | 99.7 | 99.7 | 99.7 | 99.8 | 99.8 | 99.8 | 99.0 |
| | APHA | 120 | 15 | 20 | 17 | 15 | 15 | 12 | 15 | 20 | 40 |
| Comparative Example II-3 | Recovery ratio | 10.5 | 19.1 | 29.1 | 38.8 | 48.5 | 59.2 | 68.8 | 79.2 | 90.1 | 95.2 |
| | Purity | 50.3 | 88.9 | 97.8 | 99.7 | 99.7 | 99.8 | 99.8 | 99.8 | 99.8 | 99.6 |
| | APHA | 150 | 20 | 35 | 35 | 25 | 25 | 25 | 25 | 25 | 60 |

It is clear from Table 19 that Examples II-5–8 excelled Comparative Example II-3. Specifically, the average APHA value at TEA purities exceeding 99% was 15.9, 12, 1, 16.1, and 17.0 for Examples II-5–8, and 30.0 for Comparative Example II-3, indicating the ratio of (Example II-5)/(Comparative Example II-3) to be 0.53, that of (Example II-6)/(Comparative example II-3) to be 0.41, that of (Example II-7)/(Comparative Example II-3) to be 0.52, and that of (Example II-8)/(Comparative example II-3) to be 0.57. Thus, Example II-5 brought an improvement of 47%, Example II-6 an improvement of 59%, Example II-7 an improvement of 48%, and Example II-8 an improvement of 43% respectively in the APHA value over that of Comparative Example II-3.

The entire disclosure of Japanese Patent Application Nos. JP-2003-26072 and JP-2003-171784 filed on Feb. 3, 2003 and Jun. 17, 2003 including specification, claims, drawings and summary are incorporated herein by reference in its entirety.

What is claimed is:

1. A process for producing a trialkanolamine having an APHA of not more than 40, comprising:
    producing a mixed alkanolamine by (1) a reaction of an alkylene oxide with liquid ammonia in the presence of a zeolite catalyst or (2) a reaction of an alkylene oxide with liquid ammonia in the presence of a zeolite catalyst and a reaction of an alkylene oxide with aqueous ammonia;
    removing unreacted ammonia, water, a monoalkanolamine, and a dialkanolamine from the mixed alkanolamine to obtain a mixture deprived of low-boiling substances;
    removing a high-boiling substance, which has a boiling point higher than that of the trialkanolamine, by subjecting the mixture deprived of the low-boiling substances to vacuum distillation to obtain a distillate; and
    redistilling the distillate obtained by the vacuum distillation using a distillation column without a filler to obtain the trialkanolamine.

2. A process according to claim 1, wherein the unreacted ammonia is removed by means of a pressure distillation and/or nitrogen gas bubbling.

3. A process according to claim 1, wherein the water, the monoalkanolamine, and the dialkanolamine are removed continuously or batchwise by a vacuum distillation.

4. A process according to claim 1, wherein the redistillation is performed batchwise.

5. A process according to claim 1, wherein a distillate obtained by the redistillation is grouped into an initial fraction, an intermediate fraction, and a post fraction, and the intermediate fraction is collected as a trialkanolamine product.

6. A process according to claim 5, further comprising determining the weight percentage of the trialkanolamine in the distillate before the redistilling step.

7. A process according to claim 1, wherein the reaction requires at least part of the mixed alkanolamine to be recycled.

8. A process according to claim 1, wherein the mixed alkanolamine comprises a mono-, di-, and tri-alkanolamine.

9. A process according to claim 1, wherein the trialkanolamine is triethanolamine, the alkylene oxide is ethylene oxide, the alkanolamine is ethanol amine, the monoalkanolamine is monoethanolamine, and the dialkanolamine is diethanolamine.

10. A process for refining a trialkanolamine from a mixed alkanolamine obtained by a reaction of an alkylene oxide with ammonia, comprising:
    removing unreacted ammonia, water, a monoalkanolamine, and a dialkanolamine from the mixed alkanolamine by fractional distillation to form a raw material trialkanolamine;
    adding to the raw material trialkanolamine a low-boiling compound having a boiling point less than that of the trialkanolamine prior to distillation; and
    distilling the resultant trialkanolamine using a distillation column without a filler.

11. A process according to claim 10, wherein the low-boiling compound is at least one selected from the group consisting of water; alcohols; ketones; esters; diols; and halogenated hydrocarbons.

12. A process according to claim 11, wherein the low-boiling compound is at least one selected from the group consisting of water, ethanol, methanol, propyl alcohol, isopropyl alcohol, butyl alcohol, t-butyl alcohol, acetone, methylethylketone, ethylene glycol monoacetate, ethylene glycol monoethyl ether acetate, monoethylene glycol, diethylene glycol, and carbon tetrachloride.

13. A process according to claim 10, wherein the low-boiling compound is at least one selected from the group consisting of water, a monoalkanolamine, and mixtures thereof.

14. A process according to claim 10, further comprising removing at least a portion of the unreacted ammonia by means of a pressure distillation and/or nitrogen gas bubbling prior to the fractional distillation.

15. A process according to claim 10, wherein the water, the monoalkanolamine, and the dialkanolamine are removed continuously or batchwise by a vacuum distillation.

16. A process according to claim 10, wherein the mixed alkanolamine is obtained by (1) a reaction of an alkylene oxide with liquid ammonia in the presence of a zeolite catalyst or (2) a reaction of an alkylene oxide with liquid ammonia in the presence of a zeolite catalyst and a reaction of an alkylene oxide with aqueous ammonia.

17. A process according to claim 10, wherein the mixed alkanolamine comprises a mono-, di-, and tri-alkanolamine.

18. A process according to claim 10, wherein the trialkanolamine is triethanolamine, the alkylene oxide is ethylene oxide, the alkanolamine is ethanol amine, the monoalkanolamine is monoethanolamine, and the dialkanolamine is diethanolamine.

* * * * *